United States Patent
Nambu

(10) Patent No.: US 9,031,186 B2
(45) Date of Patent: May 12, 2015

(54) X-RAY IMAGING APPARATUS INCLUDING WORK-STATE DETECTION AND X-RAY DOSAGE CONTROL

(75) Inventor: Kyojiro Nambu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 374 days.

(21) Appl. No.: 13/394,048

(22) PCT Filed: Jun. 3, 2011

(86) PCT No.: PCT/JP2011/003157
§ 371 (c)(1),
(2), (4) Date: Mar. 2, 2012

(87) PCT Pub. No.: WO2011/152070
PCT Pub. Date: Dec. 8, 2011

(65) Prior Publication Data
US 2012/0163534 A1    Jun. 28, 2012

(30) Foreign Application Priority Data

Jun. 4, 2010   (JP) ................................ 2010-129047

(51) Int. Cl.
| A61B 6/00 | (2006.01) |
| A61B 6/12 | (2006.01) |
| A61B 19/00 | (2006.01) |

(52) U.S. Cl.
CPC . *A61B 6/542* (2013.01); *A61B 6/54* (2013.01); *A61B 6/486* (2013.01); *A61B 6/487* (2013.01);
(Continued)

(58) Field of Classification Search
CPC ............ H05G 1/34; A61B 6/54; A61B 6/541; A61B 6/542; A61B 6/486; A61B 6/487
USPC .................. 378/42, 98.7, 108, 109, 110
See application file for complete search history.

(56) References Cited

U.S. PATENT DOCUMENTS

| 5,161,178 A | 11/1992 | Honda et al. |
| 5,278,887 A * | 1/1994 | Chiu et al. ................. 378/156 |

(Continued)

FOREIGN PATENT DOCUMENTS

| CN | 101119680 A | 2/2008 |
| JP | 4-109961 A | 4/1992 |

(Continued)

OTHER PUBLICATIONS

Office Action issued Feb. 18, 2014 in Japanese Patent Application No. 2010-129047.

(Continued)

*Primary Examiner* — Allen C. Ho
(74) *Attorney, Agent, or Firm* — Oblon, McClelland, Maier & Neustadt, L.L.P.

(57) ABSTRACT

An X-ray imaging apparatus according to one embodiment captures an X-ray image by irradiating a subject with X-rays from an X-ray generating means, and detecting X-rays that have penetrated the subject with an X-ray detecting means, and includes a working-state detecting means and an X-ray dosage control means. The working-state detecting means detects a plurality of types of working-state information related to the working state of the operator performing surgery on the subject. The X-ray dosage control means, based on the plurality of types of detection results detected by the working-state detecting means, controls the X-ray dosage irradiated from the X-ray generating means.

12 Claims, 20 Drawing Sheets

(52) U.S. Cl.
CPC ........... *A61B 6/12* (2013.01); *A61B 2019/5238* (2013.01); *A61B 2019/5265* (2013.01); *A61B 2019/562* (2013.01)

(56) References Cited

U.S. PATENT DOCUMENTS

| | | | | |
|---|---|---|---|---|
| 5,949,811 | A * | 9/1999 | Baba et al. | 378/108 |
| 6,041,097 | A * | 3/2000 | Roos et al. | 378/62 |
| 6,144,754 | A | 11/2000 | Okano et al. | |
| 6,229,907 | B1 | 5/2001 | Okano et al. | |
| 7,835,498 | B2 * | 11/2010 | Bonfiglio et al. | 378/115 |
| 7,851,736 | B2 * | 12/2010 | Spahn | 250/205 |
| 8,036,917 | B2 * | 10/2011 | Kariathungal et al. | 705/3 |
| 8,121,255 | B2 * | 2/2012 | Sugiyama | 378/98 |
| 2004/0007180 | A1 | 1/2004 | Yamasaki et al. | |

FOREIGN PATENT DOCUMENTS

| | | |
|---|---|---|
| JP | 5-237082 | 9/1993 |
| JP | 07 143968 | 6/1995 |
| JP | 08 275195 | 10/1996 |
| JP | 9 24042 | 1/1997 |
| JP | 10 262953 | 10/1998 |
| JP | 2000-279400 | 10/2000 |
| JP | 2001 149354 | 6/2001 |
| JP | 2003 338953 | 11/2003 |
| JP | 2004 091917 | 3/2004 |
| JP | 2008 237684 | 10/2008 |
| JP | 2008-272010 A | 11/2008 |
| JP | 2009 143373 | 7/2009 |
| JP | 2010 005326 | 1/2010 |
| JP | 2010 051742 | 3/2010 |

OTHER PUBLICATIONS

International Search Report issued on Aug. 23, 2011 in PCT/JP11/03157 filed on Jun. 3, 2011.
Combined Office Action and Search Report issued Aug. 2, 2013 in Chinese Patent Application No. 201180003246.9 with English translation of categories of cited documents.
Japanese Office Action issued Sep. 30, 2014, in Japan Patent Application No. 2010-129047.

* cited by examiner

X-RAY IMAGING APPARATUS INCLUDING WORK-STATE DETECTION AND X-RAY DOSAGE CONTROL

TECHNICAL FIELD

An embodiment of the present invention is related to an X-ray imaging apparatus.

TECHNICAL BACKGROUND

In recent years, due to advantages such as low invasiveness in relation to the subject, there has been a significant increase in techniques performed by inserting a funicular insert instrument configured by a narrow, funicular member into the body. These insert instruments include catheters as well as guide wires that are introduced together with catheters, etc. In this specification, these and other funicular insert instruments are hereinafter referred to as "wire(s)". Because wires generally absorb more X-rays than the human body, in X-ray images, they are observed as relatively clear black, narrow lines.

One example of a surgery in which wires are used is catheterization under X-ray fluoroscopy. In catheterization under X-ray fluoroscopy, a catheter is inserted into the body from an artery of the femoral region, etc., and the catheter is guided to the affected area while referring to an X-ray fluoroscopy image (moving image) displayed in real time to perform treatment.

An X-ray imaging apparatus used in catheterization under X-ray fluoroscopy irradiates X-rays for fluoroscopy to a subject into whom a catheter has been inserted, detects X-rays that have penetrated the subject, and based on the detection results, forms and displays a Real time rendering movie depicting the interior of the subject. Moreover, the X-ray imaging apparatus is configured to be able to change fluoroscopy conditions, including the X-ray dosage during fluoroscopy of the subject, based on information from input operations, and when the X-ray dosage is raised, a finer Real time rendering movie is displayed as a result. In a finer Real time rendering movie, it is possible to make the tissues inside the subject, including the blood vessels, easier to view (e.g., Patent Document 1).

In catheterization under X-ray fluoroscopy, the operator must guide the catheter to the affected area through an appropriate path through the blood vessels, which are stretched in all directions like a maze, to the affected area. Operations for doing so are performed by manipulating the part of the catheter that is outside the body. Therefore, catheterization under X-ray fluoroscopy requires expert skill.

When inserting a catheter into a desired branch at a desired bifurcation of the blood vessels, or when passing a constricted portion, first, the apical part of the catheter is inserted into the path. To do this, the operator performs very subtle operations, including appropriately combining operations such as advancing, retracting and twisting the catheter. Furthermore, if the catheter is advanced while the apical part is not appropriately inserted into the path, complications such as puncturing of the blood vessel may occur.

Moreover, when appropriately inserting the apical part of the catheter into the path, in order to make the branch or constricted portion of the blood vessel easier to observe, it is possible to confirm the position to which the guide wire should be advanced by displaying a finer X-ray fluoroscopy image. To display a finer X-ray fluoroscopy image, it is possible to occasionally supply a contrast agent from the catheter and observe the image of the contrast agent that appears for only a few seconds to confirm the position to which the guide wire should be advanced. However, because contrast agents impose a burden on the kidney function of the patient, the quantity used is limited, and it is not possible to continuously use a contrast agent during operations to insert the apical part of the catheter. Moreover, it is possible to display a finer X-ray fluoroscopy image by raising the X-ray dosage during fluoroscopy of the subject. However, in catheterization under X-ray fluoroscopy, the act of continuously irradiating the subject with large dosages of X-rays contradicts the imperative to minimize the amount of exposure of the subject.

PRIOR ART DOCUMENTS

Patent Document

[Patent Document 1] Japanese published unexamined application 2001-149354

SUMMARY OF THE INVENTION

Problem to be Solved by the Invention

In catheterization under X-ray fluoroscopy, the operator is not performing operations to insert the apical part of the catheter at all times, and may be performing other operations. At this time, the operator does not require fine X-ray fluoroscopy images, and therefore, even if the dosage of X-rays irradiated to the subject is reduced to minimize the amount of exposure of the subject, this will not interfere with the other operations.

Because the X-ray imaging apparatus is configured to be able to change the X-ray dosage during fluoroscopy of the subject based on information from input operations, in catheterization under X-ray fluoroscopy, it is possible to increase and decrease the X-ray dosage through input operations in accordance with the need for fine X-ray fluoroscopy images.

However, in catheterization under X-ray fluoroscopy, it is very bothersome for the operator to consistently perform input operations to reduce the X-ray dosage each time the operator does not require fine X-ray fluoroscopy images, and this places a psychological and physical burden on the operator, and creates the problem of adverse effects on operations for inserting the apical part of the catheter, which demand very minute operations from the operator.

Means of Solving the Invention

In order to resolve the above problems, one embodiment includes a working-state detecting means and an X-ray dosage control means. The working-state detecting means detects a plurality of types of working-state information related to the working state of the operator performing surgery on the subject. The X-ray dosage control means, based on the plurality of types of detection results detected by the working-state detecting means, controls the X-ray dosage irradiated from the X-ray generating means.

MODE FOR IMPLEMENTING THE INVENTION

Figure 1:
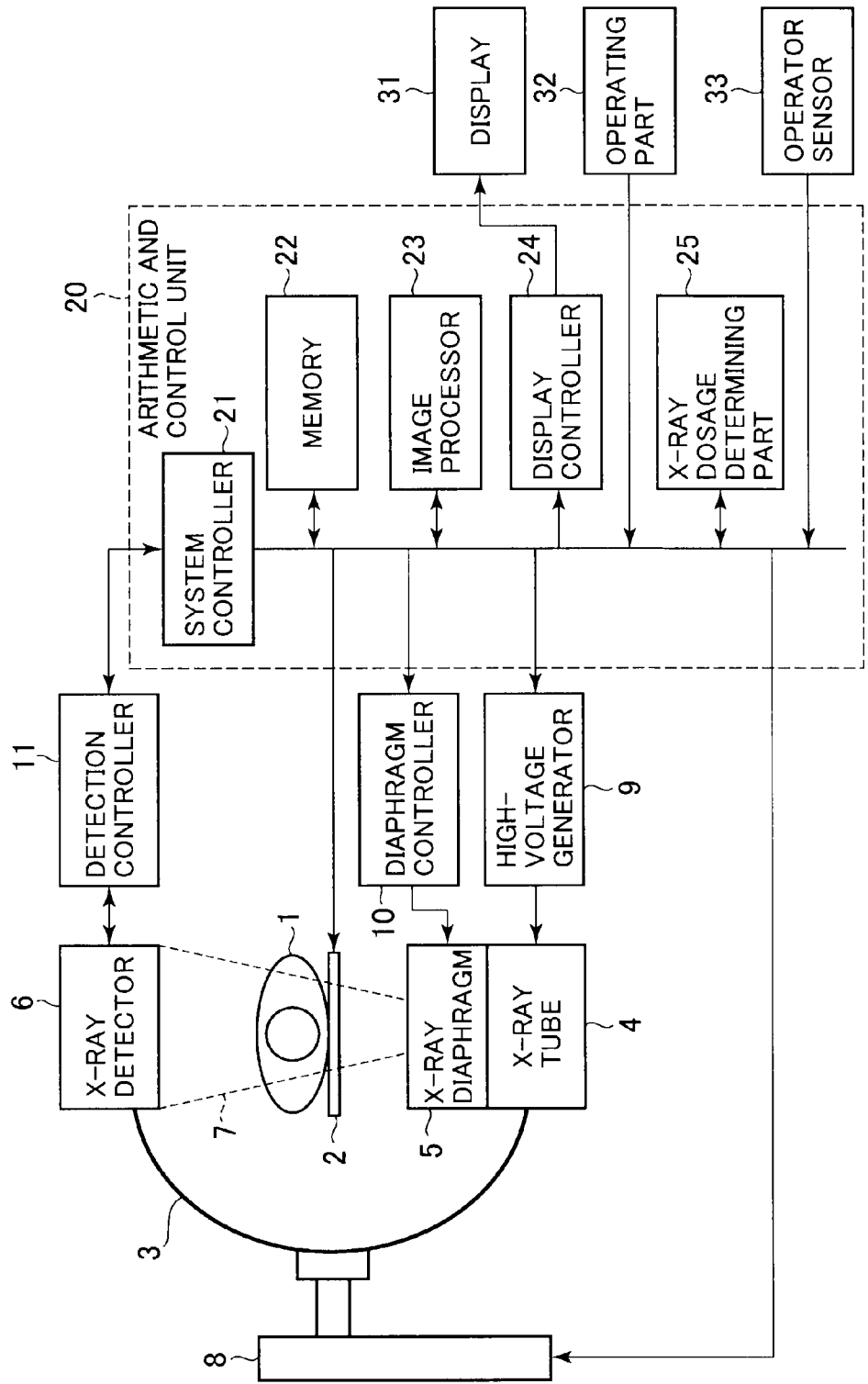
FIG. 1 is a drawing showing the overall configuration of an X-ray imaging apparatus according to a first working-state detection method.

An example of an embodiment of an X-ray imaging apparatus will be described in detail with reference to the drawings.

An X-ray imaging apparatus according to one embodiment irradiates a subject with X-rays from an X-ray generating means, detects X-rays that have penetrated the subject with an X-ray detecting means to capture an X-ray image, and includes a working-state detecting means and an X-ray dosage control means. The working-state detecting means detects multiple types of working-state information related to the working state of the operator performing surgery on the subject. Based on the multiple types of detection results detected by the working-state detecting means, the X-ray dosage control means controls the X-ray dosage irradiated from the X-ray generating means.

The X-ray imaging apparatus according to this embodiment is used for surgeries performed by inserting a wire into the body of the subject. The following provides a particularly detailed description of cases in which the X-ray imaging apparatus is applied to catheterization under X-ray fluoroscopy. In catheterization under X-ray fluoroscopy, if the operator does not require fine X-ray fluoroscopy images, this X-ray imaging apparatus keeps the amount of exposure of the subject low without imposing a burden on the operator. To do this, in catheterization under X-ray fluoroscopy, this X-ray imaging apparatus determines whether or not to reduce the current X-ray dosage, and if it makes a determination to reduce the X-ray dosage, it automatically reduces the X-ray dosage.

Information for making a determination as to whether the operator requires fine X-ray fluoroscopy images during catheterization under X-ray fluoroscopy may include the following working states of the operator. A working state 1 is the state of manipulation of an instrument (wire) by the operator, such as a state in which the instrument has been manipulated by the operator, for example. A working state 2 is the posture of the operator when the operator is looking at a display for displaying X-ray fluoroscopy images, for example. A working state 3 is biological information of the operator when the respiration of the operator is being restrained or when the operator is in a state of tension during operations to insert the apical part of a wire, which requires very minute operations from the operator. A working state 4 is actions of the operator, such as when the operator engages in conversation. A working state 5 is when the operator or an X-ray technician performs an operation to instruct the device to reduce or increase the dosage.

The working states described here are actions performed by the operator when X-rays are being irradiated by an operation of an exposure switch. Based on these types of working-state information, it is possible to detect the manipulated state of the instrument being inserted by the operator, and based on those detection results, the X-ray irradiation conditions related to the X-ray dosage of the irradiated X-rays are controlled.

The combination of the above multiple working states of the operator becomes the information for determining whether or not the operator requires fine X-ray fluoroscopy images. Consequently, this X-ray imaging apparatus determines whether or not to reduce the current X-ray dosage based on this information for making a determination.

Methods for detecting the working state of the operator as information for making a determination when the X-ray imaging apparatus determines whether or not to reduce the current X-ray dosage are described in detail.

<First Working-State Detection Method>

The first working-state detection method detects the working state of a wire handled by an operator during catheterization under X-ray fluoroscopy, based on the amount of motion of the wire. The amount of motion of the wire will be described using the amount of change in the shape of the wire as an example.

[Device Configuration]

First, the configuration of the X-ray imaging apparatus according to this embodiment will be described. An example configuration of the X-ray imaging apparatus is shown in FIG. 1. This X-ray imaging apparatus has a mechanical composition similar to that of conventional apparatuses.

The subject 1 represents the patient undergoing catheterization under X-ray fluoroscopy. The subject 1 is placed on a top board 2. The top board 2 is part of a bed device that is not shown in the drawings. The bed device is provided with a drive mechanism for moving the top board 2. The subject 1 is placed on the top board 2 by lying down. Some X-ray imaging apparatuses are provided with a standing loading table that supports the subject in an upright state, but in catheterization under X-ray fluoroscopy, treatment is normally performed for a subject supported in a supine state on the top board.

A C-arm 3 is a support member formed roughly in the shape of the letter C. An X-ray tube 4 and an X-ray diaphragm 5 are supported on one end of the C-arm 3, and an X-ray detector 6 is supported on the other end. As a result, the X-ray tube 4 and X-ray diaphragm 5, and the X-ray detector 6 are arranged as positions facing each other across the subject 1. The X-ray tube 4 is an example of the "X-ray generating means" of the present invention. Moreover, the X-ray detector 6 is an example of the "X-ray detecting means" of the present invention.

The C-arm 3 is movably supported by the drive mechanism 8. By moving the C-arm 3 under the control of an arithmetic and control unit 20, the drive mechanism 8 changes the positions and tilt angles of the X-ray tube 4, the X-ray diaphragm 5, and the X-ray detector 6.

The X-ray tube 4 generates X-rays 7 when a high voltage is applied from a high-voltage generator 9. The X-ray diaphragm 5 includes aperture blades that regulate the irradiation range (solid angle and cross-sectional shape) of the X-rays 7 generated from the X-ray tube 4. A diaphragm controller 10 moves the position of the aperture blades to change the irradiation range of the X-rays 7. Operations of the high-voltage generator 9 and the diaphragm controller 10 are controlled by the arithmetic and control unit 20.

The X-rays 7 with an irradiation range regulated by the X-ray diaphragm 5 are irradiated on the subject 1. The X-rays 7 that have penetrated the subject 1 are projected to the X-ray detector 6. The X-ray detector 6 detects the X-rays 7, converts the detection results into electrical signals, and transmits them to a detection controller 11. The detection controller 11 transmits these electrical signals to the arithmetic and control unit 20. Moreover, the detection controller 11 controls operations of the X-ray detector 6.

The X-ray detector 6 may be configured using, for example, a Flat Panel Detector (FPD) or an Image Intensifier (I.I.).

In the present embodiment, the X-ray tube 4 is controlled so as to irradiate pulse X-rays 7 at a prescribed time interval. This time interval is set to, for example, around 1/30 to 1/5 of a second (irradiation count per second of 5 to 30). Although irradiation at a maximum count of several tens per second, for example, is possible with the X-ray imaging apparatus, this level of time interval is selected to reduce the X-ray exposure of the subject 1 and the operator. As a result, moving images at a frame rate of around 5 to 30 frames per second are obtained. It is also possible to continuously irradiate X-rays instead of repeatedly irradiating pulse X-rays in this manner.

The arithmetic and control unit 20 controls each part of the X-ray imaging apparatus and executes various arithmetic processes. The arithmetic and control unit 20 has a configuration similar to that of, for example, a general computer. As an example, the arithmetic and control unit 20 is configured by including a microprocessor, a storage device (RAM, ROM, hard disk, etc.—such as memory 22), and a communication interface, etc. An operating device, an input device and a display device are connected to the arithmetic and control unit 20.

The system controller 21 in the arithmetic and control unit 20 controls each part of the X-ray imaging apparatus. Examples include the following: controlling the drive mechanism 8 to move the C-arm 3; controlling the high-voltage generator 9 to change the X-ray irradiation conditions (dosage of the X-rays 7, frame rate, tube current, etc.), thereby performing, for example, increase and decrease adjustments of the X-ray dosage described below; controlling the diaphragm controller 10 to change the irradiation range of the X-rays 7; and controlling the detection controller 11 to cause it to control the operations of the X-ray detector 6. Moreover, the system controller 21 controls each part of the arithmetic and control unit 20. The arithmetic and control unit 20 is an example of the "X-ray dosage control means" of the present invention.

An image processor 23 forms an image (digital image data) of the subject 1 based on electrical signals transmitted from the X-ray detector 6 via the detection controller 11. Moreover, the image processor 23 performs various image processes on this image. The details of the image processor 23 will be described below.

A display controller 24 receives control from the system controller and displays information on a display 31. The display 31 is configured by using a display device such as a Liquid Crystal Display (LCD) or a CRT (Cathode Ray Tube), etc.

Based on the detection results of working states output from multiple operator sensors 33, an X-ray dosage determining part 25 determines whether or not to reduce the current X-ray dosage, and if it makes a determination to reduce the current X-ray dosage, it outputs a control signal to reduce the X-ray dosage. The details of the X-ray dosage determining part 25 will be described below.

An operating part 32 is used for operating the X-ray imaging apparatus and for information input, etc. The operating part 32 is configured by including operating devices and input devices such as a keyboard, a mouse, a control panel, and a pedal operating part, etc. The pedal operating part outputs instruction signals for initiating or stopping X-ray irradiation, and outputs instruction signals for increasing or decreasing the X-ray dosage.

An operator sensor 33 detects the amount of change in the shape of a wire based on the difference between a wire image in any one frame from among multiple frames included in the moving images and a wire image in a frame from further in the past, and outputs the detection results. The operator sensor 33 is an example of the "working-state detecting means" of the present invention. The details of the operator sensor 33 will be described below.

(Image Processor)

Figure 2:
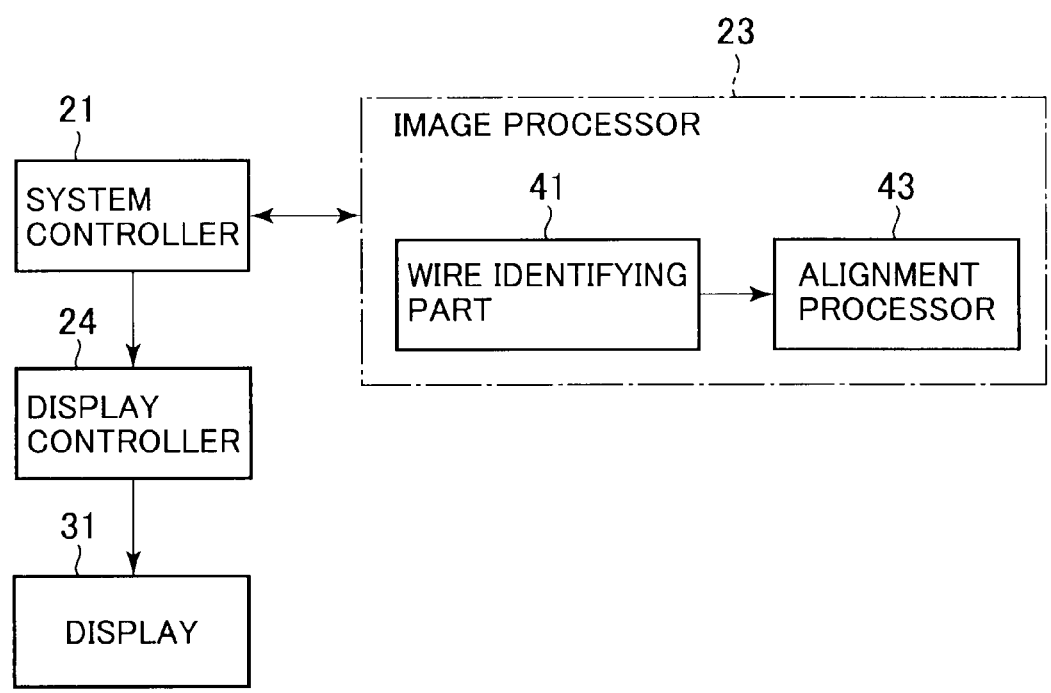
FIG. 2 is a block diagram showing the configuration of the control system of the X-ray imaging apparatus shown in FIG. 1.

An example configuration of the image processor 23 will be described with further reference to FIG. 2. The image processor 23 is provided with a wire identifying part 41 and an alignment processor 43.

The image processor 23 executes the processes described below in real time. Real-time processes in the present embodiment refer to responding to the input of electrical signals (corresponding to one frame) from the X-ray detector 6 into the arithmetic and control unit 20 by immediately executing a process on the frame and outputting (displaying) the results. As a result, it becomes possible to display the status of the wire as a moving image within a delay time that is considered to have no delay in practice.

(Wire Identifying Part)

As described above, in the present embodiment, moving images with a frame rate of approximately 5 to 30 frames per second are obtained. The wire identifying part identifies the image of the guide wire in each of the multiple frames configuring this moving image.

Here, a frame refers to each of a series of still images configuring the moving image. Moreover, the above multiple frames are not necessarily all of the frames configuring the moving image. For example, they may be multiple frames determined according to a start timing and an end timing of characteristic functions of the present embodiment (described below). Furthermore, during surgery, moving images of around several to 30 frames are continuously generated every second over a long period of time (for example, several hours), but the functions according to the present embodiment may be used for several minutes from this period, for example. The image processor 23 initiates operations when there is an instruction to initiate use of the functions according to the present invention, and executes processes such as the following. The frames subject to the processes of the image processor 23 are the series of frames acquired after the time of the instruction to initiate use.

Figure 3:
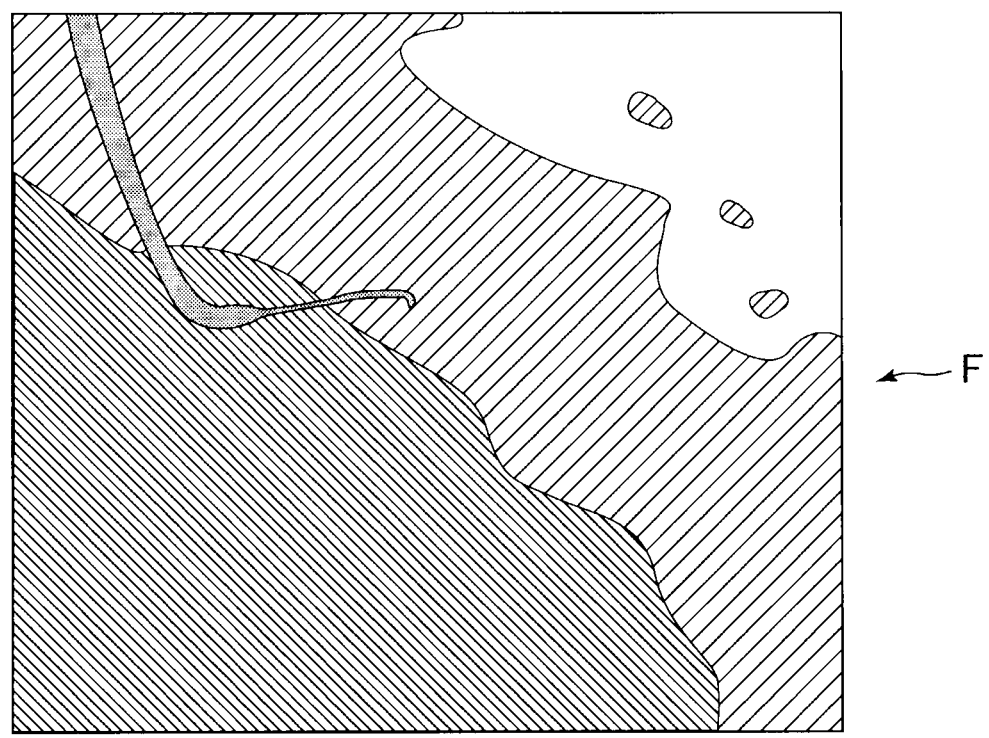
FIG. 3 is a drawing showing a frame that is displayed by the X-ray imaging apparatus shown in FIG. 1 and depicts a wire inserted into the body.

The operations of the wire identifying part 41 will be described in more detail. An example of a frame is shown in FIG. 3. Frame F shows a catheter and a guide wire inserted from the femoral artery into the coronary artery via the aorta. Generally, in an X-ray image, areas with low amounts of X-ray penetration are often depicted as black, and areas with high amounts are often depicted as white. FIG. 3 also conforms to this display method. A schematic drawing of the image shown in FIG. 3 is shown in FIG. 4.

The image C' that appears as a dim strip in the frame F is the shadow of a catheter. Moreover, the image C that appears slightly black at the position of the apical portion of the image C' of the catheter is the shadow of a guide wire. The tip of the catheter has an opening. The tip side of the guide wire is projected from this opening. Moreover, the large curvature near the center of the guide wire has occurred because the catheter has become embedded in the bifurcation from the aorta to the coronary artery. Looking at the apical portion of the image C of the guide wire, although it is slight, there is a large curvature. This is a bend that is preliminarily placed on the guide wire to make it easier to insert the guide wire into bifurcations, etc. of blood vessels. The frame F depicts this type of state.

Figure 4:
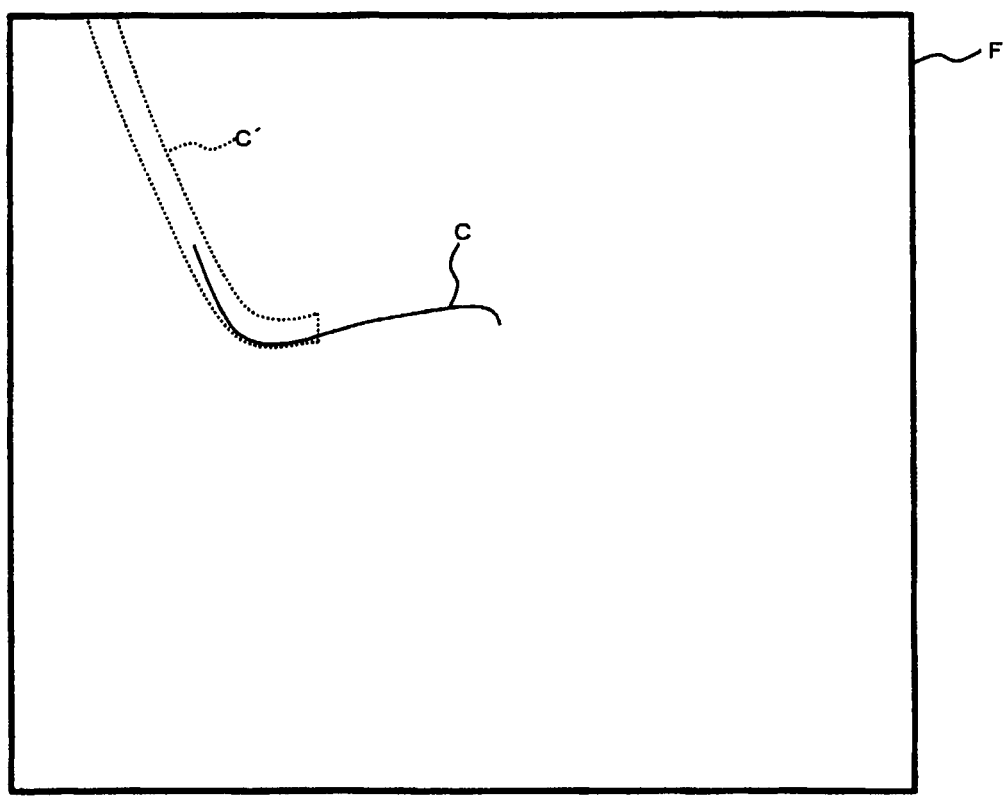
FIG. 4 is a drawing showing an outline of the frame shown in FIG. 3.

It should be noted that, in FIG. 4, images depicting body tissues such as blood vessels, organs and bones, etc. are omitted to facilitate easy viewing (the same applies to other schematic drawings). In the actual frames, complex gradation patterns corresponding to body tissues are also depicted, as shown in FIG. 3. Moreover, in the present embodiment, unless specified otherwise, images are not distinguished from their actual objects (catheter, guide wire, body tissues, etc.).

In the present embodiment, frames such as that shown in FIG. 3 are processed. In order to more easily and highly accurately identify the wire image C, first, the wire identifying part 41 performs a highlighting process to make the image C clearer. As an example of this highlighting process, there is a method of performing non-linear brightness conversion to decrease density irregularities of the wire image C, and then performing an image filtering process that extracts components with high spatial frequencies from among the various spatial-frequency components of the image. This image filtering process eliminates global, smooth gradations and leaves only local, minute variation components.

The highlighting process is not limited to the example described above. For example, it is possible to determine the details of the highlighting process appropriately in accordance with the characteristics of the X-ray imaging apparatus being used or the subject. Moreover, it is possible to realize the highlighting process by appropriately combining known image processing technology.

The wire identifying part 41 performs an appropriate pattern extraction process on the frame F and identifies the wire image C. For this pattern extraction process, it is possible to appropriately use any image processing technique, such as a threshold process on pixel values or a spatial filtering process. Moreover, the identification of the wire image C may be configured to identify the contour of the image C instead of identifying the entirety of the image C.

Mathematically, the wire is a smooth curve (three-dimensional curve) embedded in a real space (three-dimensional space). On the other hand, images obtained by the X-ray imaging apparatus are two-dimensional curves in which this three-dimensional curve is projected on a planar surface. This projection uses the position of the X-ray tube 4 (i.e., the position at which the X-rays 7 are generated) as the viewpoint, and uses the detector plane of the X-ray detector 6 as a projected planar surface. Consequently, it is possible to capture the identified wire image C as a two-dimensional curve (also represented by the symbol "C").

Figure 5:
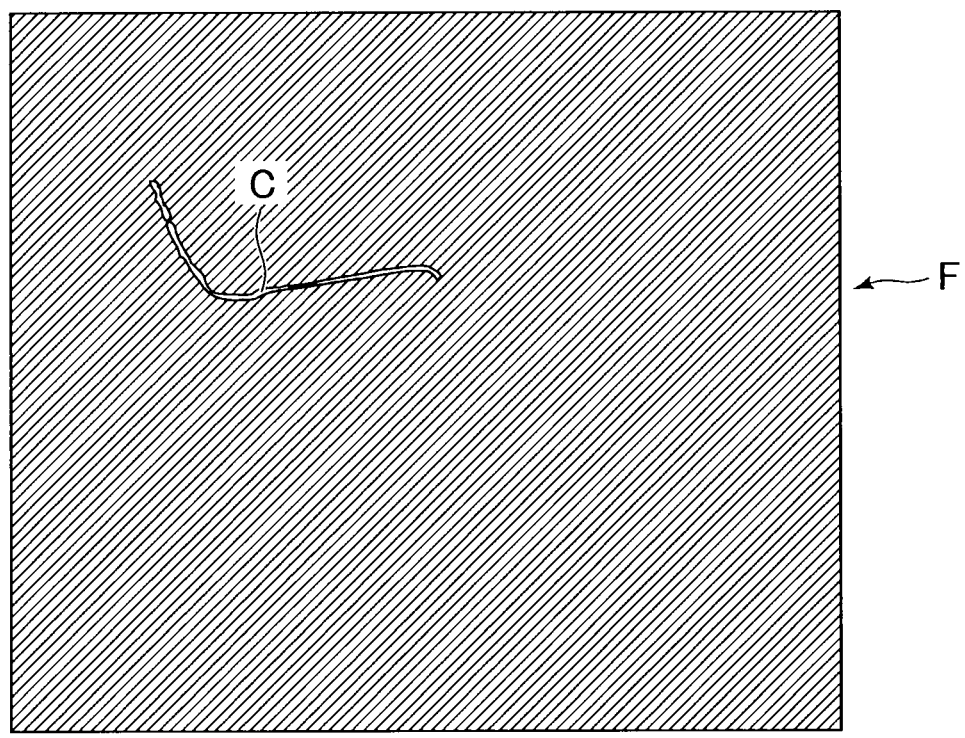
FIG. 5 is a drawing showing an image of a wire extracted from the frame shown in FIG. 3.
Figure 6:
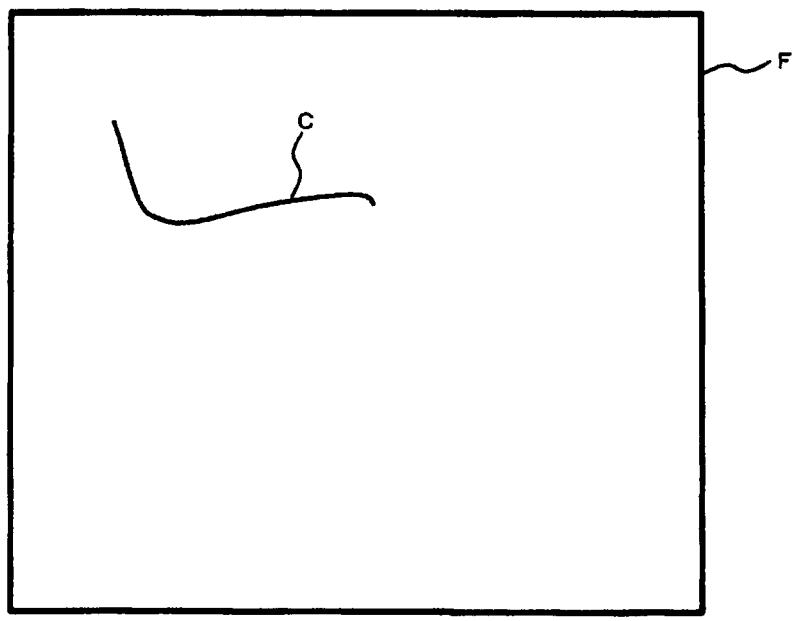
FIG. 6 is a drawing showing a two-dimensional curve based on the image of a wire shown in FIG. 5.

The wire identifying part 41 extracts the image C of the identified wire from the frame F. The alignment processor 43 represents the extracted image C as a two-dimensional curve (described later). An example of the extracted wire image C is shown in FIG. 5. Moreover, an example of a two-dimensional curve C based on the wire image C is shown in FIG. 6.

For each frame based on the electrical signals transmitted sequentially from the X-ray detector 6 at the time interval described above, the wire identifying part 41 executes the above processes in real time. As a result, multiple wire images are obtained in chronological order.

Figure 7:
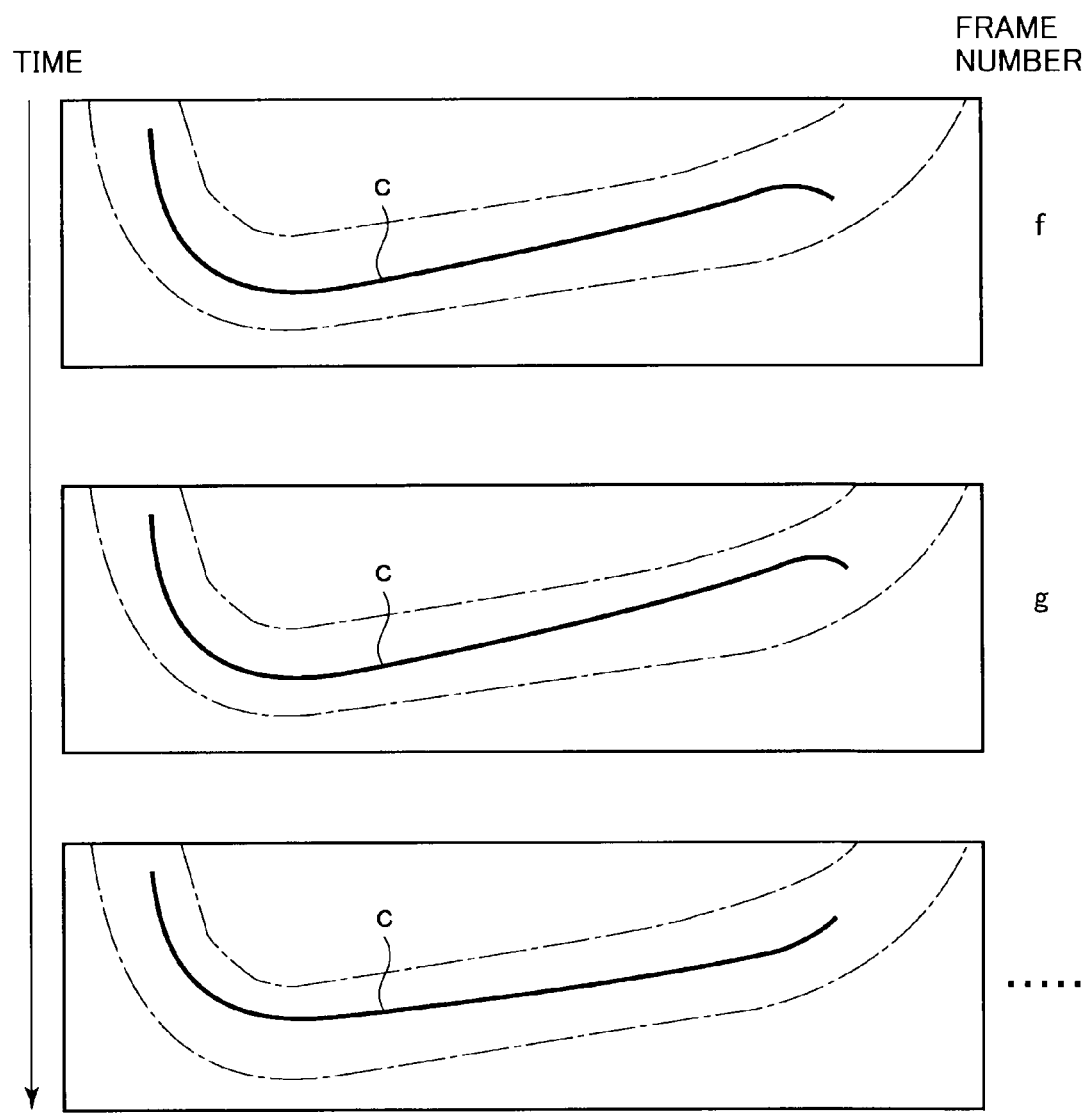
FIG. 7 is a drawing showing a two-dimensional curve based on multiple images of a wire obtained in chronological order by the X-ray imaging apparatus shown in FIG. 1.
Figure 8:
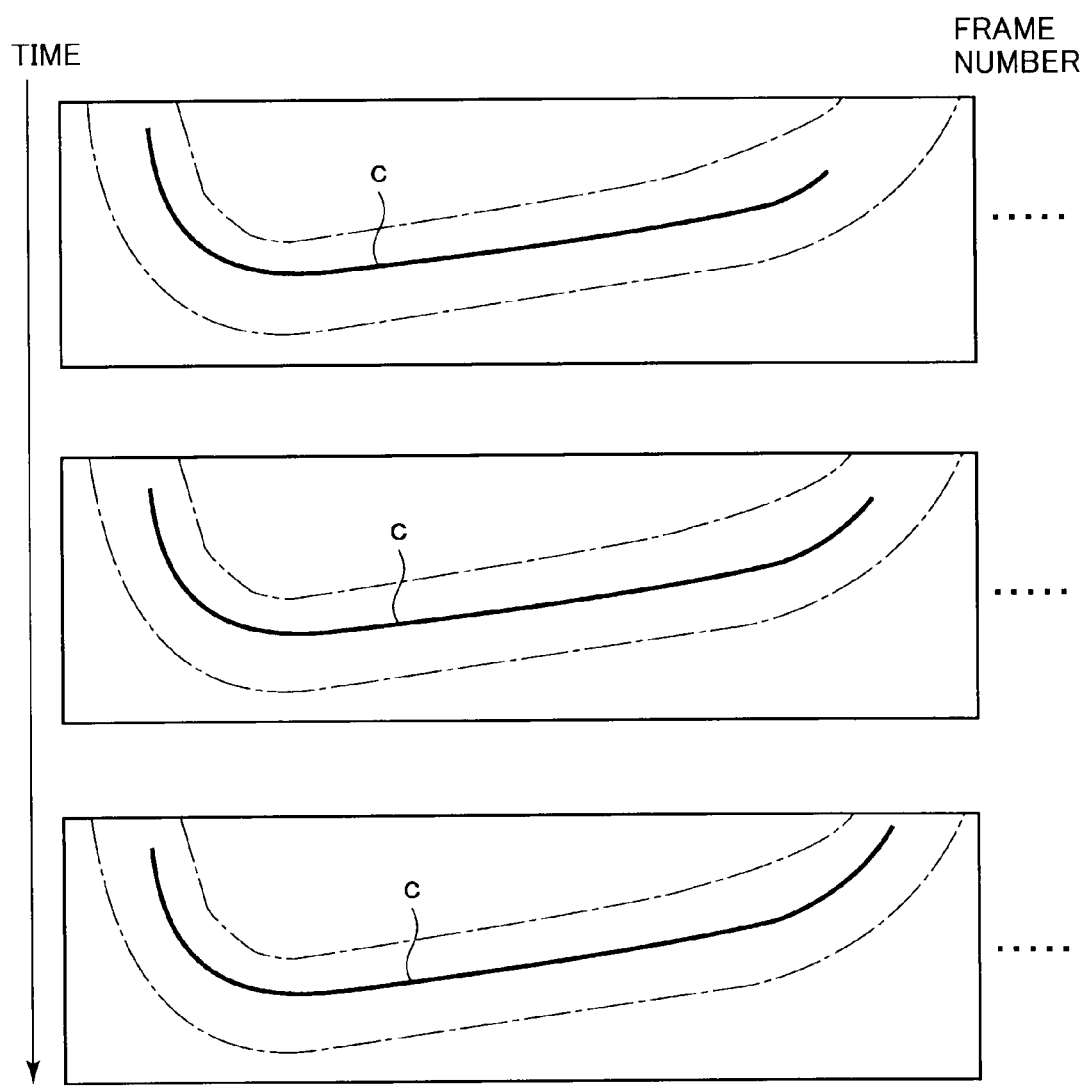
FIG. 8 is a drawing showing a two-dimensional curve based on multiple images of a wire obtained in chronological order by the X-ray imaging apparatus shown in FIG. 1.

FIG. 7 shows the two-dimensional curve C based on the wire image extracted from each of a group of temporally continuous frames in a case in which the wire has been axially rotated by a wire manipulation by the operator. Moreover, FIG. 8 shows the two-dimensional curve C based on the wire image extracted from each of a group of temporally continuous frames in a case in which the wire has been advanced by a wire manipulation by the operator. The gradual changes in the position and shape of the two-dimensional curve C are the result of movement caused by motion generated by the respiration and heartbeat, etc. of the subject 1, and of changes in shape of the wire itself caused by movement of the wire in the blood vessel.

When observing a wire inside a body, it is desirable to irradiate X-rays from a direction that is as perpendicular to the wire as possible. This is because doing so makes motion of the wire easiest to observe in the footage (i.e., in the moving images). When comparing the wire images C between two temporally adjacent frames, differences between the two are minute changes in shape or length, and although changes in the shape and position of the wire occur due to parallel displacement and rotational transfer caused by movements of the subject 1, their respective shapes are similar.

Furthermore, the apical portion of the wire may undergo drastic changes in shape due to manipulations to twist the wire or due to impact with the blood vessel wall. However, other portions reflect the shape of the blood vessel at the position where the wire is currently passing, and almost never undergo drastic changes in shape. In the present embodiment, the following processes are executed by using this fact.

(Alignment Processor)

The alignment processor 43 executes processes such as the following for each frame other than the first frame from among the series of frames subject to the application of the functions according to the present embodiment. Here, the first frame is referred to as a standard for position in processes for subsequent frames. The alignment processor 43 aligns the frame with a past frame so that the wire image C of the frame best overlaps the wire image C of the past frame. The alignment process for frames is described in detail below.

First, the alignment processor 43 obtains the two-dimensional curve C representing the shape of the wire image C in each frame (refer to FIG. 6). Here, image processes such as a thinning process is performed as needed.

Figure 9A:
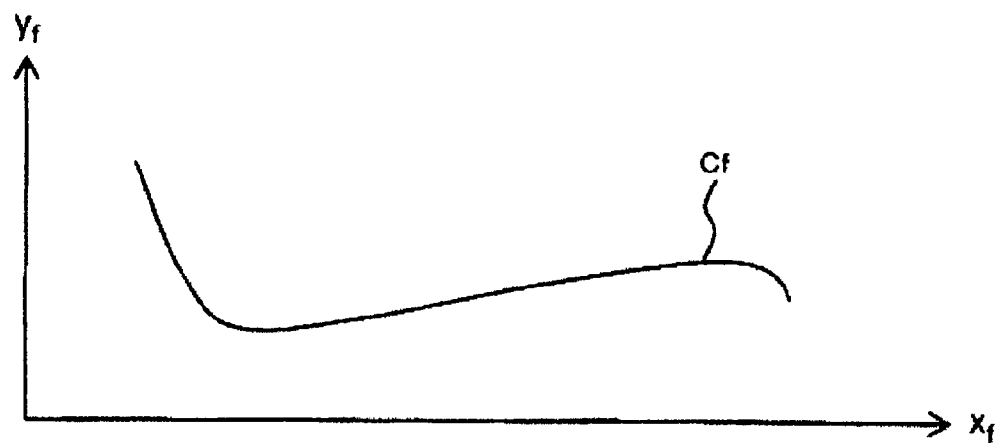
FIG. 9A is a drawing showing a two-dimensional curve based on the image of a wire in one of the two adjacent frames shown in FIG. 7.
Figure 9B:
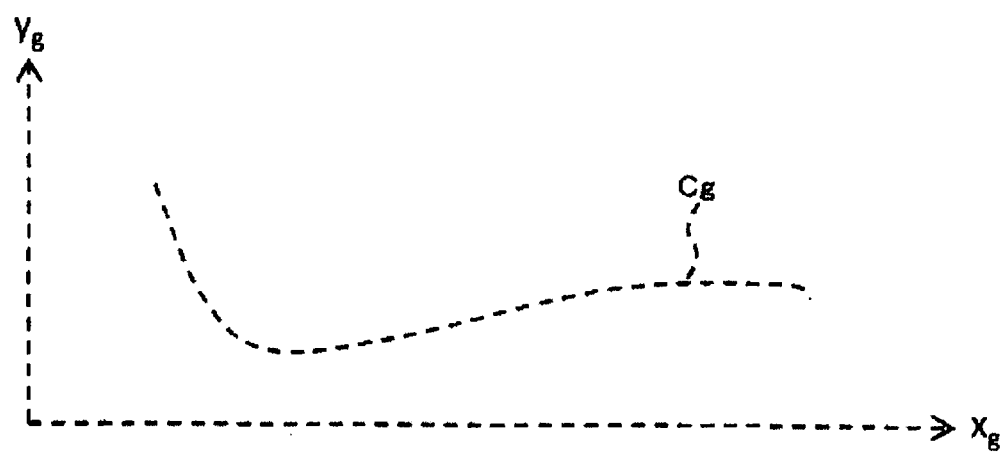
FIG. 9B is a drawing showing a two-dimensional curve based on the image of a wire in the other one of the two adjacent frames shown in FIG. 7.

First, an overview of the process of aligning two adjacent frames is described. The two-dimensional curves based on the wire images C in the adjacent frames f, g shown in FIG. 7 are shown in FIG. 9A and FIG. 9B, respectively. FIG. 9A shows a two-dimensional curve Cf corresponding to the frame f, and FIG. 9B shows a two-dimensional curve Cg corresponding to the frame g. With consideration of the overlapping described below, the two-dimensional curve Cf is represented as a solid line, and the two-dimensional curve Cg is represented as a dotted line. The same applies for the coordinate axes of each drawing.

Next, the alignment processor 43 obtains a coordinate transformation that results in the best match between the two two-dimensional curves Cf, Cg. This coordinate transformation includes parallel displacement and rotational transfer. This type of coordinate transformation may be expressed as an affine transformation. However, the affine transformation used here does not include enlargement/reduction and mirroring.

The obtained affine transformation causes the wire image C of the frame g to undergo relative parallel displacement and/or rotational transfer in accordance with the wire image C of the frame f. This affine transformation is represented by T (g, f).

Figure 10:
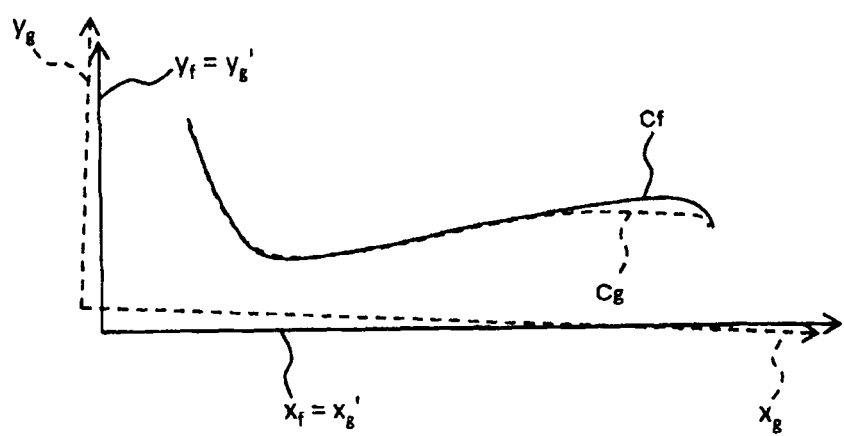
FIG. 10 is a drawing showing the superimposed state of the two two-dimensional curves shown in FIG. 9A and FIG. 9B.

When determining the affine transformation T (g, f), it is necessary to consider the effect of changes in shape caused by the movement of the wire inside the body. Therefore, instead of matching the two-dimensional curves Cf, Cg in their entirety, misalignments generated in both end portions are allowed. In particular, for the apical portion, because drastic changes in shape may occur as described above, comparatively large misalignments are allowed. For example, as shown in FIG. 10, for the apical portions of the two-dimensional curves Cf, Cg, it is not necessary to superimpose them as accurately as for other portions.

The alignment processor 43 generates weighting functions $W_f$, $W_g$ corresponding to the respective positions of the two-dimensional curves Cf, Cg.

Generally, the weight is set high for parts that are to undergo precise superimposition, and the weight is set low for parts where misalignments are allowed. For the proximity of the apical portion of the wire, because changes in shape occur easily as described above, the weight is set low. Moreover, it is possible to assign weights according to the degree of curvature at each point in the wire. For example, it is desirable to set the weight high for positions where the curvature of the wire is high. The weighting functions $W_f$, $W_g$ are generated by appropriately setting the weight for each position with consideration of these matters.

For the frame g, because superimposition is performed by applying the affine transformation T (g, f) shown in Formula (1), it is necessary to appropriately determine the parameters $\theta$, u, v. Here, the parameter $\theta$ represents the amount of rotational transfer, and the parameters u, v represent the amount of parallel displacement.

[Formula 1]

$$T(g, f) = \begin{pmatrix} \cos\theta & -\sin\theta & u \\ \sin\theta & \cos\theta & v \\ 0 & 0 & 1 \end{pmatrix} \quad (1)$$

The two-dimensional curve obtained by applying the affine transformation T (g, f) to the two-dimensional curve $(x_g, y_g)$ of the frame g is represented as $(x_g', y_g')$. By defining an evaluation of the degree of mismatch between the two-dimensional curve $(x_f, y_f)$ of the frame f and the two-dimensional curve $(x_g', y_g')$ based on an appropriate criterion as E, the parameters $\theta$, u, v are generally calculated so that the value of E becomes almost minimal.

As a more specific configuration, the following example may be used. When the distance between a point p on the two-dimensional curve $(x_f, y_f)$ and a point q that is on the two-dimensional curve $(x_g', y_g')$ and is closest to the point p is defined as D, the following formula is taken into consideration as the evaluation criterion E of the degree of mismatch.

[Formula 2]

$$E = \sum_C D W_f W_g \quad (2)$$

The sum shown in Formula (2) is obtained for all points on the two-dimensional curve $(x_f, y_f)$. Because the value of E changes when the values of $\theta$, u, and v are changed, values that keep the value of E as low as possible are searched for $\theta$, u, and v. This search is executed using a known technique, such as the nonlinear least-squares method.

An appropriate affine transformation T (g, f) is determined as described above. When this is applied to the frame g, the respective wire images C of the frame f and the frame g are almost completely superimposed, and consequently, these frames f, g are aligned. Furthermore, in the above example, the parameters of the affine transformation are calculated to keep the degree of mismatch as low as possible, but needless to say, a configuration may be used in which, conversely, the degree of matching is evaluated with an appropriate criterion and the parameters of the affine transformation are obtained so that the degree of matching is as high as possible.

In the above calculations, alignment of two adjacent frames is executed. In the present embodiment, because frames are formed sequentially in chronological order, in order to suppress motion of the wire image C in the moving images, it is necessary to sequentially accumulate the affine transformation described above. For this purpose, the alignment processor 43 executes a process such as the following.

The frame immediately before the first frame for which a process for suppressing motion is performed is defined as frame F0, and subsequent frames are sequentially defined as frame F1, F2, F3, etc. (not shown). Here, when the affine transformation applied to the frame Fn (n=1, 2, 3, etc.) is defined as $T_n$, the alignment processor 43 obtains each affine transformation $T_n$ using the following formula.

[Formula 3]

$$T_1 = T(1,0)$$

$$T_n = T(n, n-1) T_{n-1} \quad (3)$$

By sequentially applying the affine transformation $T_n$ that is sequentially obtained in this way to the corresponding frame Fn, the alignment processor 43 executes alignment of multiple sequentially obtained frames in real time.

In this way, after the following frame g is aligned to the first frame f, the frame h following the frame g is aligned to "the frame g which has been aligned to the first frame f". Consequently, the frame h is almost correctly aligned to the frame f. The same applies subsequently. In this way, it is possible to generate moving images in which the wire image C is almost still. As a result, in X-ray fluoroscopy images observed in real time during catheterization under X-ray fluoroscopy, it becomes possible to suppress movement of the wire image caused by motion of the subject.

In the alignment process described above, when the respective wire images C of the frame f and the frame g are almost completely superimposed, values that kept the evaluation criterion E for the degree of mismatch as low as possible are retrieved for the parameters θ, u, v. These parameters θ, u, v correspond to the amount of change in the shape of the wire when the operator manipulates (axially rotated, advanced, or retracted) the wire. Consequently, based on the parameters θ, u, v, it is possible to detect the amount of change in the shape of the wire.

Next, an example of actions by which the operator sensor 33 detects the amount of change in the shape of the wire based on the parameters θ, u, v is shown.

Here, in moving images obtained at a prescribed frame rate, the parameters θ, u, v retrieved when superimposing the respective wire images of the most recently obtained frame and the frame obtained immediately before are used, as are parameters θ', u', v' retrieved when superimposing the respective wire images of the frame obtained immediately before and the frame retrieved immediately before that one. Based on these parameters θ, u, v, θ', u' and v', the operator sensor 33 obtains the residual error of the mean square as shown below.

First, the operator sensor 33 obtains the mean parameter values $θ_a$, $u_a$, $v_a$ through the following calculation.

$$θ_a = (θ + θ')/2$$

$$u_a = (u + u')/2$$

$$v_a = (v + v')/2 \quad (4)$$

Next, through the following calculation, the sum of squares S of the parameters θ, u, v and θ', u', v' for the mean values $θ_a$, $u_a$, $v_a$ is obtained.

[Formula 5]

$$S = (θ - θ_a)^2 + (u - u_a)^2 + (v - v_a)^2 + (θ' - θ_a)^2 + (u' - u_a)^2 + (v' - v_a)^2 \quad (5)$$

Next, the operator sensor 33 obtains the residual error R of the mean square through the following calculation.

[Formula 6]

$$R = S/D$$

$$D = N*(n-1) \quad (6)$$

It should be noted that D represents the degree of freedom, which is the number of independently selectable variables, N represents the number of groups, which is the number of sets when observational data are coupled through one calculation, and n represents the observed value, which is the number of observational data included in a single group. Here, N=3 and n=2.

The X-ray dosage determining part 25 uses a predefined threshold value as a determination standard and determines whether the residual error R exceeds the threshold value, and when a determination result that the residual error R does not exceed the threshold value is obtained, it determines whether there is scope to reduce the current X-ray dosage. Furthermore, when the X-ray dosage determining part 25 determines whether or not there is scope to reduce the current X-ray dosage, the tube current and the frame rate are used as information for making the determination. If the tube current and the frame rate are both at the minimum values, the image quality of the X-ray fluoroscopy images will fall and the moving images will not move smoothly, and therefore, a determination is made that there is no scope to reduce the current X-ray dosage. On the other hand, if at least one of the tube current and the frame rate is not at the minimum value, a determination is made that there is scope to reduce the current X-ray dosage.

Figure 11:
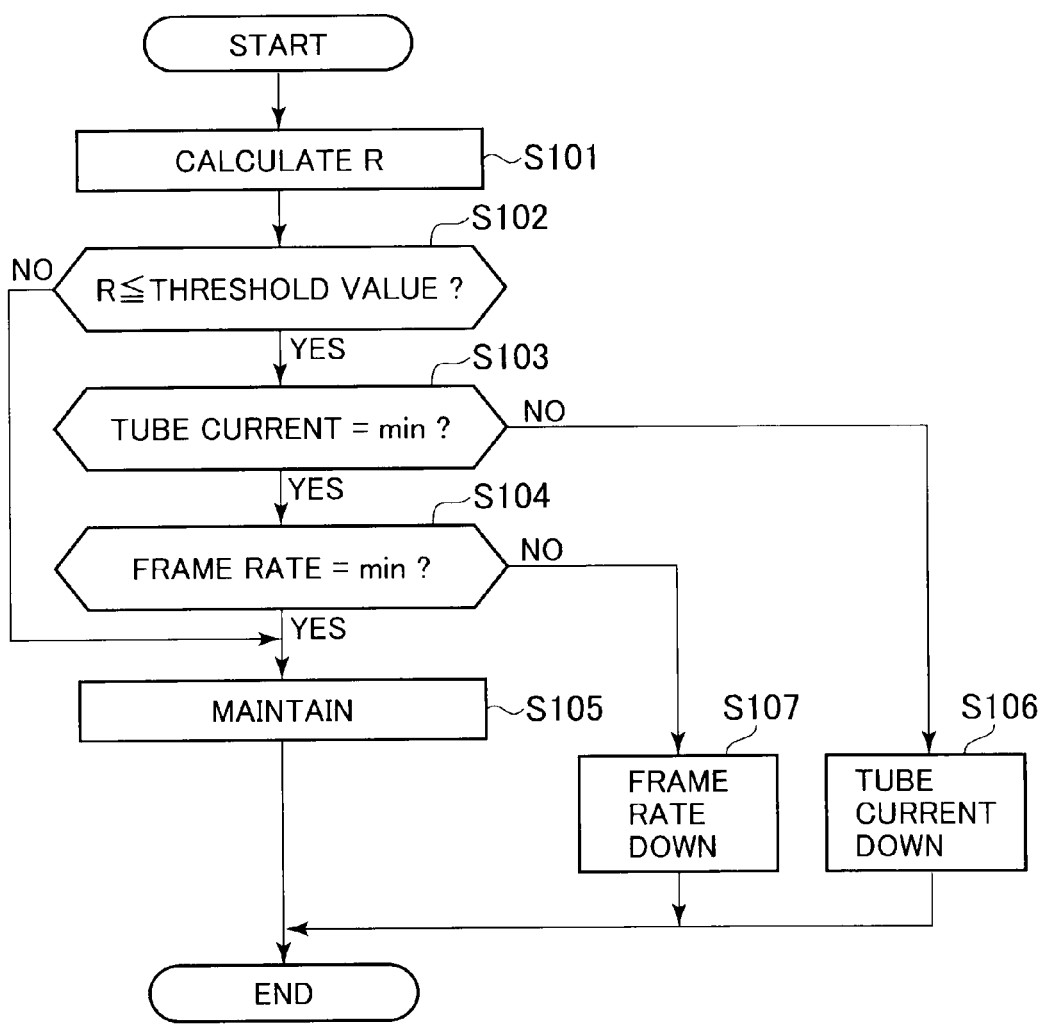
FIG. 11 is a flowchart showing one example of a determination by an X-ray dosage determining part.

The determination process by the X-ray dosage determining part 25 described above will now be described in further detail with reference to the flowchart shown in FIG. 11.

When the operator sensor 33 obtains the residual error R based on the calculations using the Formulae (4) through (6) described above (S101), the X-ray dosage determining part 25 determines whether or not the residual error R exceeds the threshold value (S102). If the operator sensor 33 determines that the residual error R exceeds the threshold value (S102: No), the system controller 21 maintains the current X-ray dosage. On the other hand, if the operator sensor 33 determines that the residual error R does not exceed the threshold value (S102: Yes), the X-ray dosage determining part 25 determines whether or not there is scope to reduce the current X-ray dosage in the following manner, for example.

The X-ray dosage determining part 25 determines whether the tube current is at the minimum value (min) (S103), and if it determines that the tube current is not at the minimum value (i.e., there is scope to reduce the current X-ray dosage) (S103: No), the system controller 21 outputs a control signal for reducing the tube current to the high-voltage generator 9 and reduces the tube current (S106). If the X-ray dosage determining part 25 determines that the tube current is at the minimum value (S103: Yes), it determines whether the frame rate is at the minimum value (min) (S104). If a determination is made that the frame rate is not at the minimum value (i.e., there is scope to reduce the current X-ray dosage) (S104: No), the system controller 21 outputs a control signal for lowering the frame rate to the high-voltage generator 9 and lowers the frame rate (S107).

On the other hand, if the X-ray dosage determining part 25 determines that the tube current is at the minimum value (S103: Yes) and determines that the frame rate is at the minimum value (S104: Yes), because there is no scope to reduce the current X-ray dosage, the system controller 21 maintains the current X-ray dosage without outputting a control signal for reducing the tube current and a control signal for lowering the frame rate to the high-voltage generator 9 (S105).

Furthermore, the X-ray dosage determining part 25 synthesizes the detection results of multiple working states using detection methods of other working states (described below), and determines whether or not there is scope to reduce the current X-ray dosage. The details of the method for making a comprehensive determination are described in the section <Method of synthesizing detection results of multiple working states> described below.

In the present embodiment, in the alignment process, by performing prescribed calculations based on the retrieved parameters $\theta$, u, v, the amount of change in the shape of the wire is detected, and therefore, the operator sensor 33 may be configured mainly with software.

<Second Working-State Detection Method>

The second working-state detection method detects the working state by using, as information for making a determination on the working state of the wire manipulated by the operator, the results of detecting sounds and vibrations generated when the wire is manipulated, the results of detecting motion of the hand of the operator manipulating the wire, or the detection results from an acceleration sensor attached to the operator. Here, a wire is described as an example of the insert instrument. The wire is inserted into the subject using an adaptor.

Here, an example is described in which the results of detecting sounds and vibrations generated when the wire is manipulated are used as information for making a determination on the manipulated state of the wire. When the wire is manipulated, a valve (not shown) provided inside the adaptor is rubbed with the wire, and sounds and vibrations in a specific frequency band are generated. If the generation of the sounds and vibrations is frequent, it is possible to presume that the operator is manipulating the wire.

Figure 12:
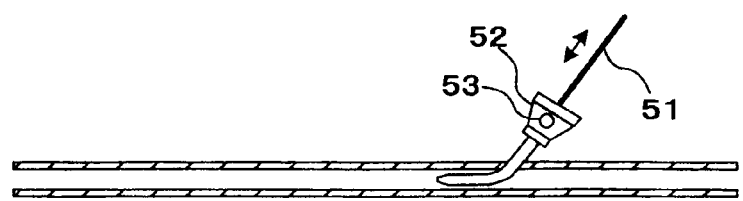
FIG. 12 is a drawing showing an example in which a contact microphone attached to an adaptor is used as an operator sensor according to a second working-state detection method.
Figure 13:
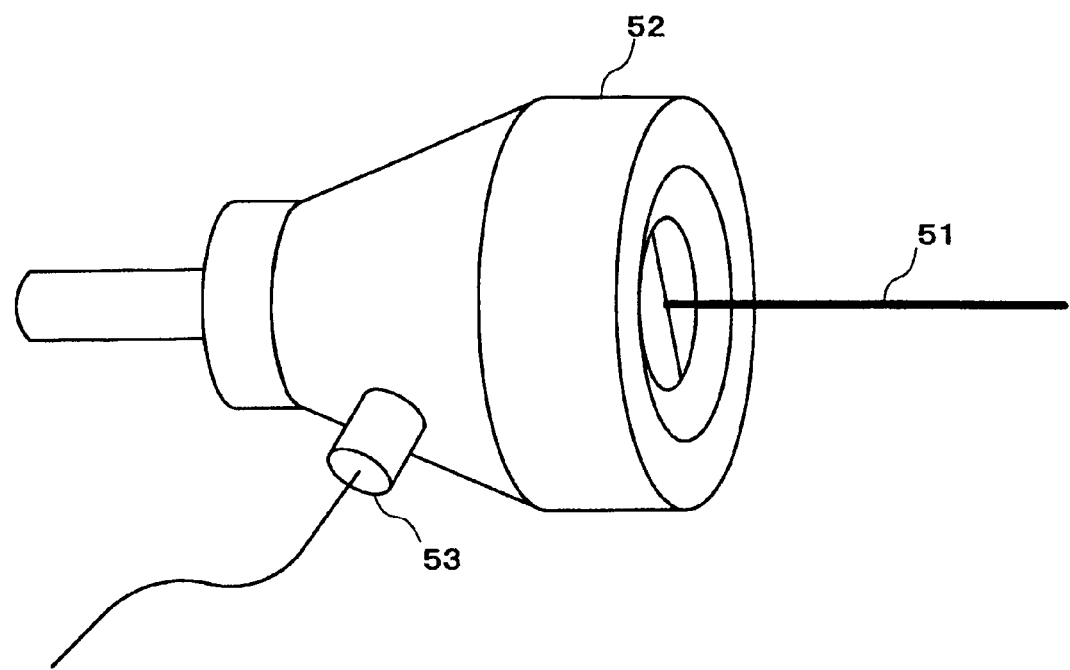
FIG. 13 is a drawing showing an enlargement of the adaptor part shown in FIG. 12.

The details of the present embodiment will now be described with reference to FIG. 12 and FIG. 13. FIG. 12 is a drawing showing an example using a contact microphone 53 attached to the adaptor 52, and the direction of manipulation of the wire 51 is indicated by the arrow. FIG. 13 is a drawing showing an enlargement of the adaptor part. Sounds and vibrations from the wire 51 grazing the valve are detected by the contact microphone 53 attached to the adaptor 52, and the frequency of wire manipulation is detected. The X-ray dosage determining part 25 determines whether or not this frequency exceeds a predefined threshold value (e.g., N times in 10 seconds), and if it determines that the threshold value is not exceeded, it determines whether there is scope to reduce the current X-ray dosage. This is because it is deduced that the operator is not manipulating the wire and does not require fine X-ray fluoroscopy images.

Next, an example is described in which the results of detecting motion of the hand of the operator manipulating the wire are used as information for determining the manipulated state of the wire. Using, for example, an infrared-reflection motion sensor attached to the adaptor, motion of the hand of the operator is detected near the adaptor, the mean amount of motion of the hand of the operator is obtained every second, and the number of times that the mean value meets or exceeds a specific amount is detected. Using a predefined threshold value (e.g., N times per 10 seconds) as a judgment standard, the X-ray dosage determining part 25 determines whether or not the detected number of times exceeds the threshold value, and if it determines that the threshold value is not exceeded, it determines whether or not there is scope to reduce to the current X-ray dosage. This is because it is deduced that the operator is not manipulating the wire and does not require fine X-ray fluoroscopy images. Here, examples of an infrared-reflection motion sensor include those in which multiple pyroelectric elements are arranged within a detection range set at the focal length of an infrared condenser lens, and motion of the detection subject (i.e., the hand of the operator) is detected as changes in the quantity of electricity in the pyroelectric elements.

It should be noted that, for the operator sensor 33 that detects motion of the hand of the operator manipulating the wire, instead of an infrared-reflection motion sensor, an acceleration sensor may be attached to the hand of the operator. In this case, the acceleration sensor detects the number of times that the acceleration meets or exceeds a specific amount, and the X-ray dosage determining part 25 uses a predefined threshold value (e.g., N times per 10 seconds) as a judgment standard. Here, examples of an acceleration sensor include those that detect positional changes caused by acceleration as changes in diaphragm position by using piezoresistant elements.

<Third Working-State Detection Method>

The third working-state detection method uses the results of detecting the posture of the operator as information for determining the working state of the operator.

As an example of detection results of the posture of the operator, the results of detecting whether or not the operator is viewing a display (the display 31) for displaying X-ray fluoroscopy images may be used. Generally, when the operator approaches the display displaying X-ray fluoroscopy images, or when the operator faces the direction of the display displaying X-ray fluoroscopy images, it may be deduced that the operator is looking carefully at the X-ray fluoroscopy images and that the operator requires fine X-ray fluoroscopy images. As an example of information used for determining whether or not the operator has approached the display displaying X-ray fluoroscopy images, measurements may be taken using a sensor, such as a camera, attached to the display. There are the detection results of the position of the operator from the perspective of the display. Moreover, as an example of information for determining whether or not the operator is facing the direction of the display displaying X-ray fluoroscopy images, there are the detection results of the area of the face of the operator facing the display, and the detection results of the orientation of the face of the operator relative to the display. Furthermore, a determination as to whether the operator is viewing the display for displaying X-ray fluoroscopy images may be made by combining any two or more of these detection results as information for making a determination.

Here, an example is described in which the detection results of the position of the operator relative to the display are used as information for determining whether or not the operator has approached the display displaying X-ray fluoroscopy images. The position of the operator relative to the display is detected using an ultrasonic sensor attached to the display. As long as the distance between the display and the operator can be detected, the location for attaching the ultrasonic sensor is not limited to the display, and any location where the relative positions of the display and the operator can be grasped may be used. Furthermore, examples of ultrasonic sensors include those that transmit ultrasound waves from the sensor head, receive ultrasound waves reflected from the subject (i.e., the face of the operator) through the sensor head, and measure the time between the transmission and reflection of the ultrasound waves to detect the position of the subject.

Moreover, the device that detects the position of the operator relative to the display is not limited to an ultrasonic sensor, and may be, for example, a camera with a facial recognition function, for example. The direction from this camera with a facial recognition function to the face of the operator is detected, and based on the detection results, the distance from the screen of the display to the position of the face of the operator is calculated. As an image recognition function, the image processing function described in, for example, Japanese published unexamined application Hei 8-275195, in which a face candidate region is detected by detecting a skin-color region that is characteristic of the face using color-difference images. Furthermore, this camera with a facial recognition function may be one that simply identifies the color of the skin of the operator and detects the position of the face of the operator (i.e., the position of the location where the face of the operator is present) in the image.

Generally, when the face of the operator approaches the display, it is deduced that the operator requires fine X-ray fluoroscopy images. Moreover, when the face of the operator becomes distant from the display (becomes distant along a direction perpendicular to the screen of the display, or becomes distant in a direction at an angle relative to the direction perpendicular to the screen of the display), it can be deduced that the operator does not require fine X-ray fluoroscopy images. Consequently, using the results of the distance from the screen of the display to the position of the face of the operator as information for making a determination, the X-ray dosage determining part 25 uses a predefined threshold value (e.g., 1.5 m) as a judgment standard and determines whether or not the obtained result exceeds the threshold value, and if the threshold value is exceeded, it determines whether there is scope to reduce the current X-ray dosage. This is because it is deduced that the face of the operator is distant from the display and that fine X-ray fluoroscopy images are not required.

<Fourth Working-State Detection Method>

The fourth working-state detection method uses the results of detecting whether or not the operator is facing the direction of the display displaying X-ray fluoroscopy images as information for determining the working state of the operator.

Figure 14:
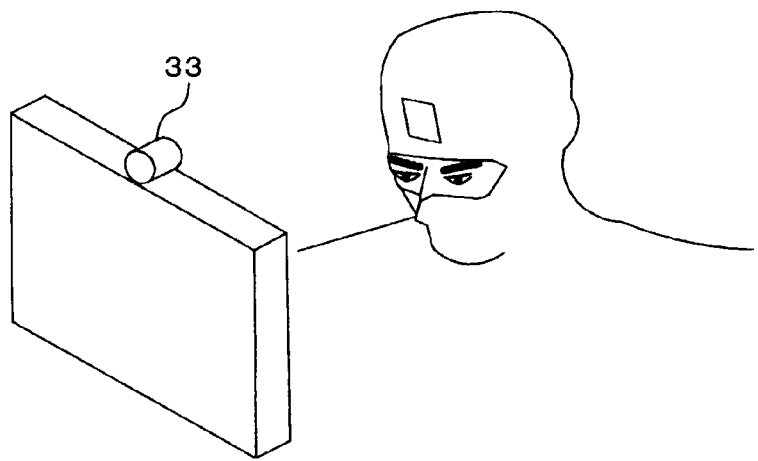
FIG. 14 is a drawing showing an example in which a camera attached to a display is used as an operator sensor according to a fourth working-state detection method.

An example will be described in which the orientation of the face of the operator or his/her line of sight is detected as working-state information. An example is described in which detection results of the area of the face of the operator relative to the display are used as detection results for whether or not the operator is facing the direction of the display displaying X-ray fluoroscopy images. The orientation of the face of the operator relative to the display is detected using a camera attached on or near the display. The camera has the image recognition function described earlier. Because the operator is wearing a surgical gown and a mask with a color different from the skin color, the camera identifies the color of the skin of the operator, identifies the position of the color of the skin in the image, and is able to detect the area of the face. If the area of the face is small, it is deduced that the operator is not directly facing the direction of the display. The camera attached to the display and the operator wearing a surgical gown and mask are shown in FIG. 14. Due to the surgical gown and mask, only the areas around the eyes and the nose of the face of the operator are exposed, and the remaining parts are covered. The exposed regions around the eyes and the nose are hereinafter referred to as the "exposed region". The area of the exposed region from the perspective of the camera is detected.

Figure 15:
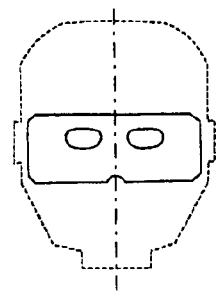
FIG. 15 is a drawing showing the exposed region when the operator faces the display directly.
Figure 16:
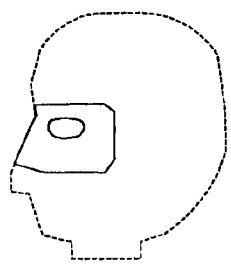
FIG. 16 is a drawing showing the exposed region when the operator does not face the display directly.

The exposed region when viewed from the camera is described with reference to FIG. 15 and FIG. 16. FIG. 15 is a drawing showing the exposed region in a case in which it is deduced that the operator is directly facing the direction of the display, and the contour shape of the exposed region shown enclosed in a solid line is an approximately rectangular shape that is lengthwise in the width direction of the face. FIG. 16 is a drawing showing the exposed region in a case in which it is deduced that the operator is not directly facing the direction of the display, and the contour shape of the exposed region shown enclosed in a solid line is an approximately rectangular shape, but the width direction of the face is shorter compared to the case shown in FIG. 15. The area of the exposed region when viewed from the camera becomes smaller as the operator faces the display more indirectly. Consequently, using the results of detecting the area of the exposed region as information for making a determination, the X-ray dosage determining part 25 uses a predefined threshold value (e.g., 50%) as a judgment standard and determines whether or not the ratio of the value of the area of the current exposed region relative to the maximum value of the area of the exposed region (i.e., the value of the area of the exposed region indicating that the operator is directly facing the direction of the display) is below the predefined threshold, and if it determines that it is below the threshold value, it determines whether or not there is scope to reduce the current X-ray dosage. This is because it is deduced that the operator is not facing the direction of the display and does not require fine X-ray fluoroscopy images.

Furthermore, instead of the area of the exposed region, it is possible to detect the exposed region, extract the contour of this exposed region, and use this contour as information for making a determination. With the contour of the exposed region, the image of the exposed region becomes large when the operator approaches the display, and the image of the exposed region becomes small when the operator becomes distant from the display. Therefore, within the contour, using, for example, the length between the lower margin of the cap and the upper margin of the mask (i.e., the vertical length of the approximately rectangular shaped contour) as a standard, the image that is the subject of comparison is enlarged or reduced so that the length thereof becomes equivalent in both images, and the contour after the size adjustment is used as information for making a determination. This image adjustment is also effective when using the area of the exposed region as information for making a determination.

<Fifth Working-State Detection Method>

The fifth working-state detection method uses detection results of the orientation of the face of the operator relative to the display that are obtained based on detection results of the eyes (iris and sclera) of the operator as information for determining the detection results of whether or not the operator is facing the direction of the display displaying X-ray fluoroscopy images. By using the detection results of the eyes (iris and sclera) of the operator, it is possible to detect the orientation of the face of the operator without being affected by variations in the size and shape of the face of the operator or variations in the way in which the surgical gown and mask are worn.

Figure 17:
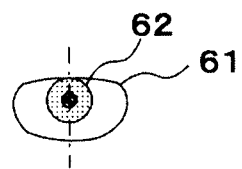
FIG. 17 is a drawing showing an image of an eye when the operator faces the display directly in a fifth working-state detection method.
Figure 18:
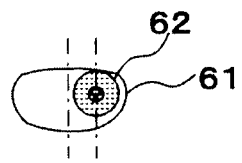
FIG. 18 is a drawing showing an image of an eye when the operator does not face the display directly.

In the detection of the orientation of the face of the operator, the region of the eyes (iris and sclera) of the operator is extracted using a camera that is attached to or near the display and has a characteristics-detecting mechanism. For the characteristics-detecting mechanism, the characteristics-detecting mechanism described in Japanese published unexamined application 2004-91917 that extracts the pupil positions and the contours of the iris regions from an image is used, for example. For example, the respective regions of the irises (pupils and irises) and the sclera extracted by the characteristics-detecting mechanism are shown in FIG. 17 and FIG. 18. As shown in FIG. 17, in the eye region indicating that the operator is presumed to face the direction of the display, the center of gravity of the iris region 62 is positioned on or near the center line of the width direction (i.e., the direction from the inner corner to the outer corner of the eye) of the sclera region 61. Moreover, as shown in FIG. 18, in the eye region indicating that the operator is presumed not to face the direction of the display, the center of gravity of the iris region 62 is positioned away from the center line of the width direction of the sclera region 61. Consequently, the X-ray dosage determining part 25 uses the results of detecting the position of the center of gravity of the iris region relative to the center line of the width direction of the sclera region as information for making a determination, and using a predefined threshold value (e.g., 5 mm) as a judgment standard, it determines whether or not the distance between the position of the center of gravity of the iris region and the center line of the width direction of the sclera region exceeds the threshold value, and if it determines that the threshold value has been exceeded, it determines whether or not there is scope to reduce the current X-ray dosage. This is because it is deduced that the operator is not facing the direction of the display and does not require fine X-ray fluoroscopy images.

<سixth Working-State Detection Method>

The sixth working-state detection method uses detection results of a target worn by the operator as information for determining the detection results of the orientation of the face of the operator relative to the display. As a result, based on reflected light, etc. from glasses used by the operator, even if the conditions for the acquisition of images of the eyes of the operator are not good, it is possible to accurately detect the orientation of the face of the operator.

As the target worn by the operator, an example is described in which a reflection marker attached on the median line of the cap or mask, etc. of the operator is used. The reflection marker is, for example, a flexible sheet formed into a rectangular shape, and is a reflective layer composed of metallic thin film of aluminum, etc. formed on the surface of the sheet through, for example, sputtering or an evaporation method, etc. An infrared light source that irradiates infrared light at the reflection marker is mounted on or near the display, and furthermore, a camera that has the frontal region (i.e., a region to which the screen is faced, that is within a specific distance from the screen) of the screen of the display as its imaging field is likewise mounted on or near the display.

Figure 19:
FIG. 19 is a drawing showing a reflection marker attached to the operator in a sixth working-state detection method.
Figure 20:
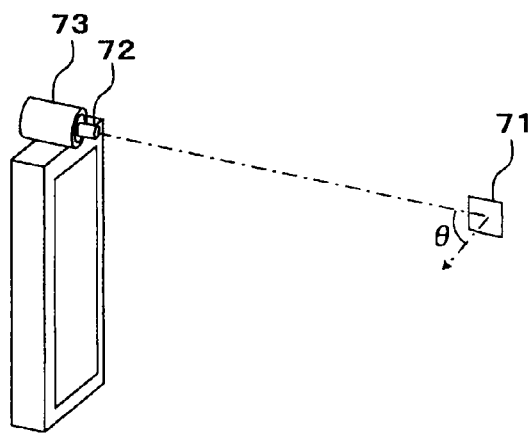
FIG. 20 is a drawing showing an operator sensor and a reflection marker.

For example, as shown in FIG. 19, a reflection marker 71 is mounted on the median line of the cap of the operator. Then, as shown in FIG. 20, the reflection marker 71 mounted on the cap (not shown) of the operator is detected by an infrared light source 72 and a camera 73 mounted on the display. $\theta$ is the angle of the reflected infrared light relative to the incident light (i.e., the sum of the incident angle and the reflection angle).

Figure 21:
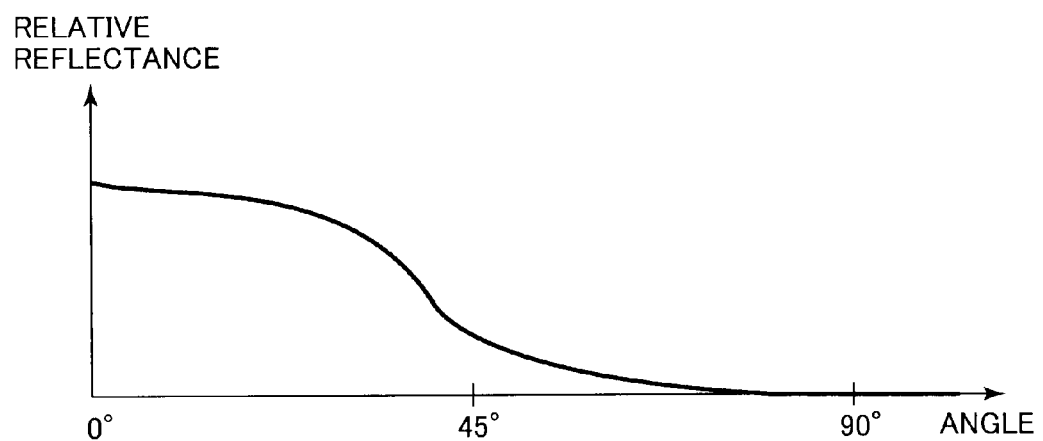
FIG. 21 is a graph showing the relationship between the angle θ and the relative reflectance with regard to the reflection marker.

Generally, because the reflection marker faces the display more directly when detected amount (by the camera 73) of reflected infrared light from the reflection marker is greater, when the detected amount is great, it is possible to deduce that the operator is directly facing the display. Consequently, the X-ray dosage determining part 25 detects the intensity of the reflected light from the reflection marker, and using the results of detecting the relative reflectance (i.e., the ratio of the intensity of the current reflected light relative to the intensity of the reflected light when directly faced) detected from the detection results as information for making a determination, it uses a predefined threshold value (e.g., 30%) as a judgment standard and determines whether or not the relative reflectance is below the threshold value, and if it determines that it is below the threshold value, it determines whether there is scope to reduce the current X-ray dosage. This is because the operator is not facing the direction of the display, and it is deduced that fine X-ray fluoroscopy images are not required. FIG. 21 is a graph showing the relationship between the angle $\theta$ and the relative reflectance. FIG. 21 shows how the relative reflectance is reduced as the angle $\theta$ goes from 0° (the angle when the operator is directly facing the display) to 90° (the angle when the operator is facing exactly laterally from the display).

(Variation)

An example using relative reflectance as information for making a determination has been described above, but the present embodiment is not limited to this. When the sum of the luminance of the pixels corresponding to the image of the reflection marker captured by the camera is great, it can be deduced that the operator is more directly facing the display. Consequently, the X-ray dosage determining part 25 detects the sum of the luminance of the reflection marker, uses the results of detecting the ratio of the sum of the luminance from the detection results (i.e., the ratio of the current sum of the luminance relative to the sum of the luminance when faced directly) as information for making a determination, and using a predefined threshold value (e.g., 30%) as a judgment standard, it determines whether or not the ratio of the sum of the luminance is below the threshold value, and if it determines that it is below the threshold value, it determines whether or not there is scope to reduce the current X-ray dosage. This is because it is deduced that the operator is not facing the direction of the display and does not require fine X-ray fluoroscopy images.

Figure 22:
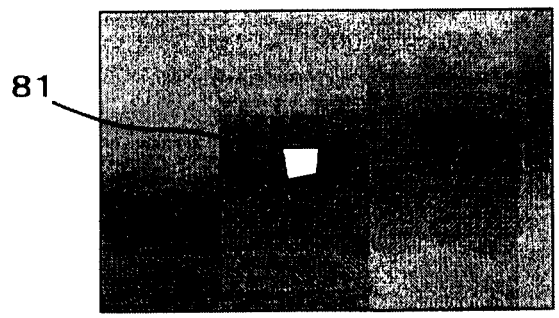
FIG. 22 is a drawing showing an image of the reflection marker when the operator faces the display directly in a variation of the sixth working-state detection method.
Figure 23:
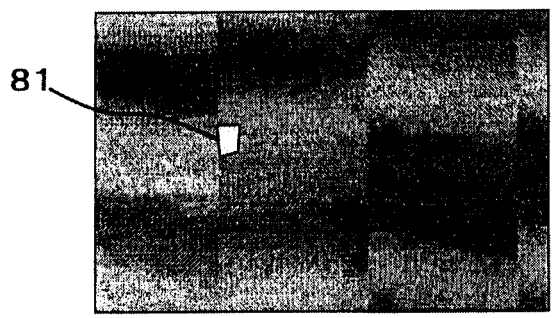
FIG. 23 is a drawing showing an image of the reflection marker when the operator does not face a liquid crystal display directly.

FIG. 22 shows an image of a reflection marker in a case in which it is deduced that the operator is directly facing the display, and the shape of the image 81 of the reflection marker that is shown with highly luminous pixels is almost a copy of the contour shape of the reflection marker. FIG. 23 shows an image of a reflection marker in a case in which it is deduced that the operator is not directly facing the display, and the shape of the image 81 of the reflection marker is narrow in the horizontal direction relative to the contour shape of the reflection marker, and the luminance of the pixels forming the image 81 is lower than the luminance forming the image 81 shown in FIG. 22. Consequently, the image of the reflection marker when it is deduced that the operator is directly facing the display is larger than the image of the reflection marker when it is deduced that the operator is not directly facing the display, and the luminance of the pixels forming the image is also higher.

In the third through sixth working-state detection methods described above, the operator sensor 33 detects whether or not the operator is viewing the display as the posture of the operator. However, the operator sensor 33 that detects the posture of the operator is not limited to this.

<Seventh Working-State Detection Method>

The seventh working-state detection method uses, as information for determining the working state of the operator, detection results from the operator sensor 33 for detecting whether or not body motion of the operator is frequent.

In catheterization under X-ray fluoroscopy, when performing wire manipulations requiring very precise operations, the operator normally does so without making great changes in posture, and the frequency of body motion of the operator is therefore low. Consequently, in catheterization under X-ray fluoroscopy, if body motion of the operator is frequent, the operator is not performing wire manipulations, and it may therefore be deduced that the operator does not require fine X-ray fluoroscopy images. Focusing on this point, the operator sensor 33 for detecting whether or not body motion of the operator is frequent is provided.

As an example of using the results of detecting whether or not body motion of the operator is frequent as information for making a determination, detection results for detecting the barycenter of the operator by using a pressure sensor mat spread below the feet of the operator are described. Here, "body motion" includes, for example, the operator bending his/her upper body frontward and sideways, as well as the operator changing direction or moving their standing position, and does not include motions typical of wire manipulation, in which mainly only the hands and arms are moved while keeping the upper body still and without changing direction. The pressure sensor mat detects pressure from the feet of the operator as a two-dimensional pressure distribution pattern. The X-ray dosage determining part 25 acquires a two-dimensional pressure distribution pattern in an interval of a fixed time (e.g., 0.1 second), creates pressure distribution pattern images of several (e.g., 30) patterns acquired over a preceding predefined time (e.g., the past 3 seconds), and obtains the barycenter of the operator based on the pressure distribution pattern image. Here, as an example of the pressure sensor mat, the pressure-receiving surfaces of semiconductor pressure sensors are arranged in the pressure-receiving range, and pressure applied thereto is detected as changes in the quantity of electricity.

Figure 24:
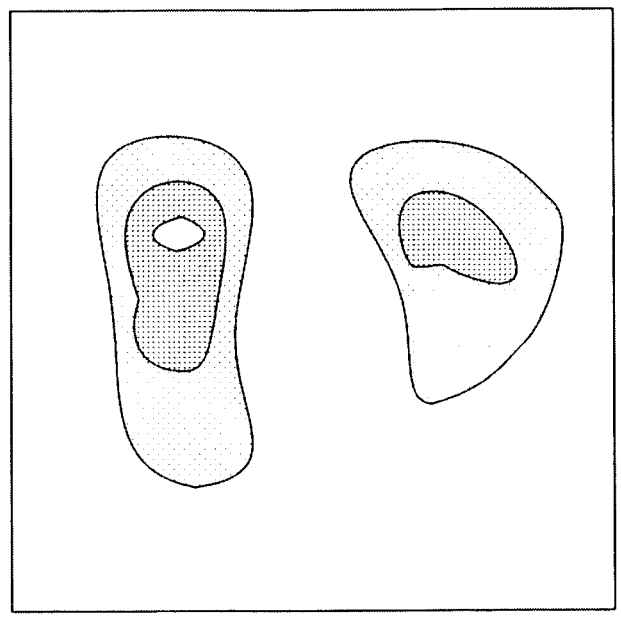
FIG. 24 is a drawing showing an operator sensor according to a seventh working-state detection method.
Figure 25:
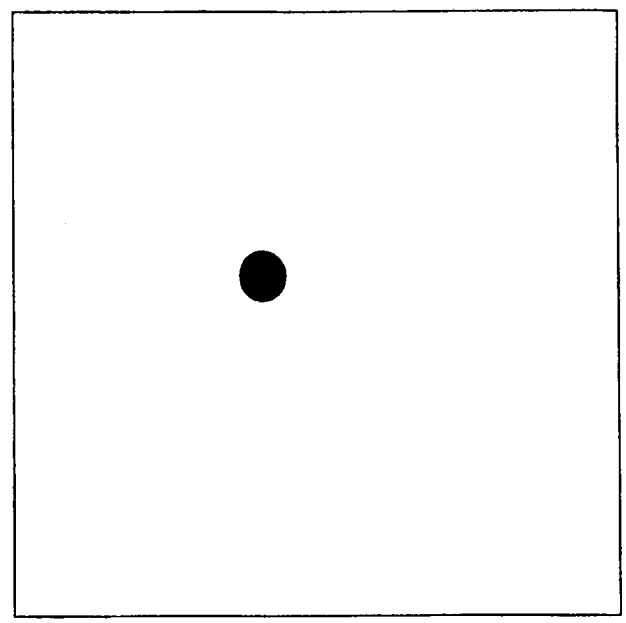
FIG. 25 is a drawing showing the barycentric position on a pressure sensor mat.

Next, further details are described with reference to FIG. 24 and FIG. 25. FIG. 24 shows a pressure distribution pattern image of the entirety of both feet. The pixels forming the pressure distribution pattern image shown in FIG. 24 have pressure values. The pressure distribution pattern of the left foot has 3 constant-pressure lines connecting pixels with the same pressure values, while the pressure distribution pattern of the right foot has 2 constant-pressure lines, showing that the operator is applying their weight on their left foot. Based on the barycenter of the pressure values related to the left foot obtained based on the pressure values of the pixels in the pressure distribution pattern of the left foot, and on the barycenter of the pressure values related to the right foot obtained based on the pressure values of the pixels in the pressure distribution pattern of the right foot, the barycenter of the pressure values of the image in the pressure distribution pattern of the entirety of both feet (i.e., the barycenter of the operator) is obtained. FIG. 25 indicates the position of the obtained barycenter of the pressure values (i.e., the barycenter of the operator) with a black circle.

For example, for multiple barycentric positions collected in the past 3 seconds, a statistical process is performed and the variation (standard deviation) is obtained. When the standard deviation is great, it may be deduced that large body motion has occurred. Consequently, the X-ray dosage determining part 25 uses a predefined threshold value (e.g., a standard deviation of 20) and determines whether or not the standard deviation of the barycentric position of the operator exceeds the threshold value. If the X-ray dosage determining part 25 determines that the standard deviation of the center position of the operator exceeds the threshold value, it determines whether or not there is scope to reduce the current X-ray dosage. This is because it is deduced that the operator has engaged in a large body motion (e.g., the operator has moved by bending their upper body forward or sideways) and does not require fine X-ray fluoroscopy images.

<Eighth Working-State Detection Method>

The eighth working-state detection method uses detection results from the operator sensor 33 for detecting biological information of the operator as information for determining the working state of the operator. Here, biological information refers to information in relation to movement, etc. that occurs in a living body based on stimulation.

The operator sensor 33 according to the third through seventh embodiments described above detects the posture of the operator as the working state of the operator. This is because the working state of the operator during catheterization under X-ray fluoroscopy reveals itself in the posture of the operator manipulating the wire while viewing the display. The working state of the operator during catheterization under X-ray fluoroscopy also reveals itself as biological information indicating a tense state, such as the restraining of respiration during wire manipulation. Consequently, the operator sensor 33 may detect biological information as the working state of the operator. Here, biological information refers to information regarding movement, etc. that occurs in a living body based on stimulation.

In catheterization under X-ray fluoroscopy, if the operator restrains their respiration, it is deduced that the operator is performing precise manipulations of the wire and requires fine X-ray fluoroscopy images. Therefore, the state of restraint of respiration of the operator is used as biological information.

As one example of the operator sensor 33, a stethoscopic microphone (skin-contact microphone) is attached to the operator, and collects and records heartbeat data. Moreover, as another example of the operator sensor 33, an ECG telemeter may be attached to the operator and configured to wirelessly collect and record an electrocardiogram.

Figure 26:
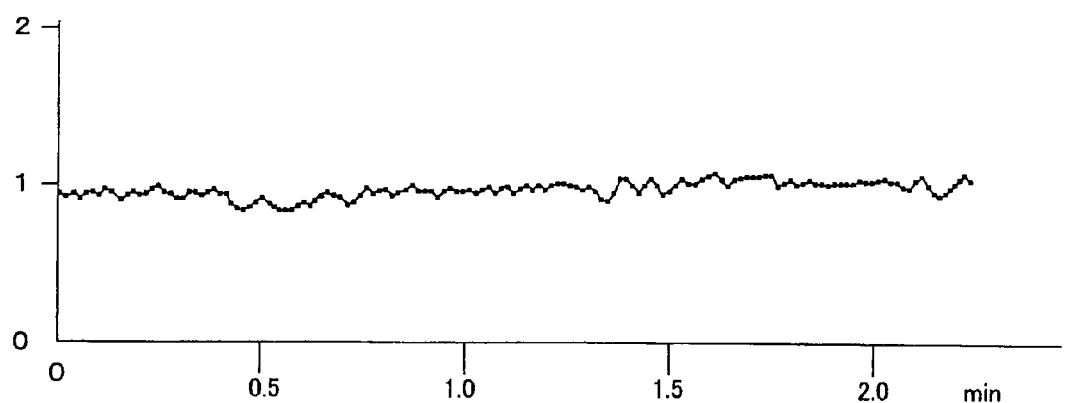
FIG. 26 is a diagram showing the heart rate of the operator when the operator is not manipulating a wire in an eighth working-state detection method.
Figure 27:
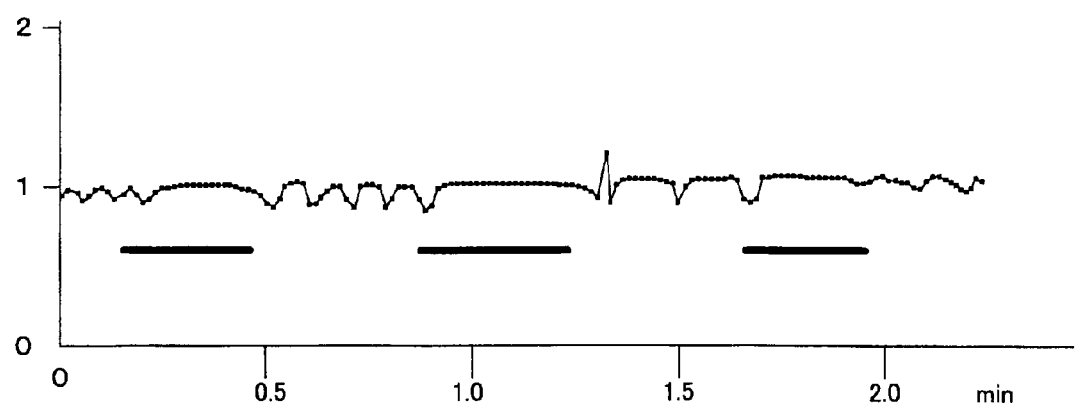
FIG. 27 is a diagram showing the heart rate of the operator when the operator is manipulating a wire.

The relationship between respiration and heart rate will be described further with reference to FIG. 26 and FIG. 27, in which the vertical axis is the cardiac cycle and the horizontal axis is the time axis. FIG. 26 shows a cardiac cycle during normal respiration, and the cardiac cycle changes in all time periods and there are no time periods in which the cardiac cycle becomes almost constant. FIG. 27 shows a cardiac cycle when respiration is restrained, and there is a time period (the underlined part) where the heart rate becomes almost constant and a time period where the cardiac cycle does not become almost constant.

The fact that the heart rate changes due to respiration is well known. It is likely that for any operator, it is necessary to breathe shallowly or stop breathing (i.e., restrain respiration) when performing precise manipulations. In other words, if the state in which respiration is restrained (the state indicated by the underline in FIG. 27) lasts for a long time period, this is a likely candidate for the performance of precise operations. When respiration is restrained, the heart rate becomes almost constant.

Therefore, the operator sensor 33 detects fluctuations (standard deviation) in the heart rate of the operator during a predefined time that has passed (e.g., the past 10 seconds). Using a predefined threshold value (e.g., a standard deviation of 20) as a judgment standard, the X-ray dosage determining part 25 determines whether the standard deviation of the heart rate exceeds the threshold value. If the X-ray dosage determining part 25 determines that the standard deviation of the heart rate exceeds the threshold value, it determines whether or not there is scope to reduce the current X-ray dosage. This is because it is deduced that the operator is not performing precise manipulations of the wire and does not need to carefully observe the display 31, and does not require fine X-ray fluoroscopy images.

(Variations)

In the eighth working-state detection method, an example was described in which the results of detecting whether or not the operator has restrained their respiration are used as biological information of the operator. However, in catheterization under X-ray fluoroscopy, when the operator manipulates the wire, because very precise manipulations are required of the operator when the operator manipulates the wire, the operator enters a tense state and the effects thereof are revealed in the biological information of the operator. The tense state of the operator is related to the necessity of fine X-ray fluoroscopy images. Consequently, the results of detecting biological information of the operator revealing the effects of a tense state may be used as the biological information of the operator detected by the operator sensor 33. Examples of biological information of the operator revealing the effects of a tense state include the results of detecting whether or not the operator is in a tense state by detecting the brain waves, pupil diameter, frequency of blinking, degree of perspiration in the skin of the palms or the soles of the feet, or skin temperature of the operator. It should be noted that the reason for detecting the degree of perspiration in the skin of the palms or the soles of the feet is that there are high numbers of sweat glands in the palms and the soles of the feet that perspire during a tense state.

A variation of the eighth working-information detection method described above will now be described. In the present variation, an example is described in which the brain waves of the operator are used as biological information of the operator. The main types of brain waves are $\alpha$ waves, $\beta$ waves, and $\theta$ waves, and the brain waves become $\beta$ waves with a frequency of 13 Hz or more in a tense state, and become $\alpha$ waves with a frequency of less than 13 Hz as a state of relaxation is entered. Consequently, it is possible to detect the brain waves of the operator using the operator sensor 33 and to use the detected results as information for determining whether or not the operator is in a tense state.

The operator sensor 33 is attached to the operator and detects the brain waves of the operator, and the X-ray dosage determining part 25 uses the results of detecting the brain waves of the operator as information for making a determination, and using a predefined threshold value (e.g., 10 Hz) as a judgment standard, determines whether or not the results of detecting the brain waves of the operator exceed the threshold value, and if it determines that the threshold value is exceeded, it determines whether or not there is scope to reduce the current X-ray dosage. This is because it is deduced that the operator is not in a tense state and that they are not manipulating the wire.

Next, another variation is described in which the degree of perspiration in the skin of the palms or the soles of the feet of the operator is used. As described above, when the operator is in a tense state, the amount of sweat generated from the skin of the palms or the soles of the feet of the operator increases. Therefore, the operator sensor 33 that detects perspiration is attached to the operator, and the degree of perspiration occurring from the palms, etc. is detected at a prescribed time interval as moisture content or electric potential. Examples of the operator sensor 33 that detects the degree of perspiration include that disclosed in Japanese published unexamined application Hei 7-143968.

Consequently, the X-ray dosage determining part 25 uses the results detected by the operator sensor 33 as information for making a determination, and using a predefined threshold value (e.g., electric potential or moisture content), determines whether or not the degree of perspiration exceeds the threshold value, and if it determines that the degree of perspiration does not exceed the threshold value, it determines whether or not there is scope to reduce the current X-ray dosage. This is because it is deduced that the operator is not in a tense state and does not require fine X-ray fluoroscopy images.

In the above variations, when detecting the biological information of the operator, the operator sensor 33 attached to the operator is used, but a variation using the operator sensor 33 not attached to the operator will now be described. In this variation, the pupil diameter of the operator is used as the biological information of the operator. It is known that the pupil diameter becomes greater during a tense state compared to a relaxed state. Consequently, if the maximum pupil diameter during a relaxed state is set as a threshold value, the pupil diameter of the operator is detected by the operator sensor 33, and it is determined that the pupil diameter does not exceed the threshold value, a determination is made as to whether or not there is scope to reduce the current X-ray dosage. This is because it is deduced that the operator is not in a tense state, is not manipulating the wire, and does not require fine X-ray fluoroscopy images.

Examples of the operator sensor 33 that detects the pupil diameter of the operator include that disclosed in Japanese published unexamined application Hei 10-262953. The operator sensor 33 includes, for example, a camera attached on or near a display. Using the camera, a facial image of the operator is acquired at a prescribed time interval, and the acquired facial image of the operator is image processed to extract the shape of the pupils. It is possible to detect the pupil diameter from the extracted shape of the pupils. Here, a predefined threshold value is detected and stored, the result of detecting the pupil diameter of the operator using the operator sensor 33 is compared with the threshold value, and the result of the comparison is used as information for making a determination.

The X-ray dosage determining part 25 uses the result of the comparison as information for making a determination, and using whether or not a predefined threshold (e.g., 90%) is exceeded as a judgment standard, if it determines that the result of the comparison does not exceed the threshold value, it determines whether or not there is scope to reduce the current X-ray dosage. This is because it is deduced that the operator is not in a tense state, is not manipulating the wire, and does not require fine X-ray fluoroscopy images.

Next, another variation using the operator sensor 33 that is not attached to the operator will be described. In this variation, blinks of the operator are used as the biological information of the operator. Generally, the frequency of blinking is normally 15 to 20 times per minute (the cycle between each blink is 3 to 4 seconds). The cycle of blinks decreases when viewing something with concentration. Because the operator should carefully view the display during wire manipulation requiring precise operations, the cycle of blinks should become longer.

Examples of the operator sensor 33 that detects the blinks of the operator include that disclosed in Japanese published unexamined application 2003-338952. The operator sensor 33 includes, for example, a camera attached on or near a display. The operator sensor 33 continuously monitors the region of the eyes of the operator, and detects blinks based on whether or not the dark part (iris) of the eyes becomes smaller. The operator sensor 33 detects the time from the detection of one blink to the detection of the following blink (i.e., the cycle of blinks).

Consequently, the X-ray dosage determining part 25 uses the cycle of blinks as information for making a determination, and using a predefined threshold value (e.g., a cycle of blinks of 3 seconds) as a judgment standard, if it determines that the cycle of blinks does not exceed the threshold value, it determines whether or not there is scope to reduce the current X-ray dosage. This is because it is deduced that the operator is not carefully viewing the display and does not require fine X-ray fluoroscopy images.

<Ninth Working-Information Detection Method>

The ninth working-information detection method uses detection results from the operator sensor 33 for detecting the behavior of the operator as information for determining the working state of the operator.

Here, the behavior of the operator includes the frequency of conversation between the operator and staff at a medical site and the amount of motion of the operator. During catheterization under X-ray fluoroscopy, if the frequency of conversation between the operator and staff is high, or if the amount of motion of the operator is high, it is deduced that precise manipulations of the wire are not being performed and that fine X-ray fluoroscopy images are not required.

First, as the operator sensor 33 that detects the frequency of conversation, the contact microphone described in Japanese published unexamined application 2010-5326, for example, is used. Using this microphone that is attached to the operator, the loudness of sounds ((decibels) (dB)) is detected instead of audio. If, for example, the mean value of the loudness of sounds over the past 3 seconds exceeds a threshold value, the X-ray dosage determining part 25 deems that a conversation has occurred, obtains the ratio of the time spent on conversation within the past 20 seconds, uses the obtained ratio of the conversation as information for making a determination, and using a predefined threshold value (e.g., 50%) as a judgment standard, determines whether or not the obtained ratio of the conversation exceeds the threshold value, and if it determines that the threshold value has been exceeded, it determines whether or not there is scope to reduce the current X-ray dosage. This is because it is deduced that the frequency of conversation is high, that wire manipulations are not being performed, and that fine X-ray fluoroscopy images are not required. Furthermore, it is also possible to simply use the mean value of the loudness of sounds over the past 3 seconds as information for making a determination, use a predefined threshold value (e.g., 50 dB) as a judgment standard, determine whether or not the mean value of the loudness of sounds over the past 3 seconds exceeds the threshold value, and if it is determined that the threshold value has been exceeded, determining whether or not there is scope to reduce the current X-ray dosage. Moreover, the operator sensor 33 that detects the frequency of conversation is not limited to a contact microphone, and a microphone that collects sounds from the operator and his/her surroundings may be used. If multiple microphones with directivity are arranged facing the operator and the multiple microphones collect sound, the collected sound is deemed to be sounds from the operator and their surroundings, and it is deduced that the operator is engaged in a conversation.

Furthermore, instead of these types of microphones, the operator sensor 33 that detects the frequency of conversation may be an ECG telemeter. In other words, using an ECG telemeter attached to the operator, variations in the heart rate are detected, and when the heartbeats become noncyclical, it is deemed that irregular respiration is occurring and that a conversation is taking place. The operator sensor 33 detects the frequency spectrum of chronological changes in the cardiac cycle of the operator over a predefined time in the past (e.g., the past 20 seconds). Using a predefined threshold value as a judgment standard, the X-ray dosage determining part 25 determines whether or not spectral components generated by normal respiration exceed the threshold value, and if it determines that the threshold value is not exceeded, it determines whether or not there is scope to reduce the current X-ray dosage. This is because it is deduced that the frequency of conversation is high, and that the operator is not performing wire manipulations and does not require fine X-ray fluoroscopy images.

Next, for the operator sensor 33 that detects motions of the operator, and example using the medical-site display system described in the above Japanese published unexamined application 2010-5326 is described. To briefly describe this system, an imaging device is placed in a medical site and captures video of the medical site. Moreover, RF tags are attached to staff, including the operator, and transmit staff identification information. A receiving device is provided in the medical site. Using this, it is possible to not only record the medical site as footage but also to identify staff and their present positions and to identify and display the staff in the medical site in the recorded footage. By using this system, it is possible to easily and chronologically detect whether or not the operator has entered the frontal region (i.e., a region to which the screen is faced, that is within a specific distance from the screen) of the screen of the display, as well as how the operator is moving within the frontal region.

Using the results of detecting the frequency of motion of the operator within the frontal region as information for making a determination, a determination is made as to whether the detection results (motion of the operator) exceeds a predefined threshold value. If it is determined that the frequency of motion of the operator exceeds the threshold value, the X-ray dosage determining part 25 determines whether or not there is scope to reduce the current X-ray dosage. This is because it is deduced that the frequency of motion of the operator is high, that wire manipulations are not being performed, and that X-ray fluoroscopy images are therefore not required.

Furthermore, if the operator does not enter the frontal region, or if the operator exits the frontal region, the X-ray dosage determining part 25 determines whether or not there is scope to reduce the current X-ray dosage. This is because it is deduced that the operator has become very distant from the display and therefore does not require X-ray fluoroscopy images.

Next, for the operator sensor 33 that detects motions of the operator, a position encoder of the bed or the X-ray gantry may be used. If the operator is manipulating the bed or the X-ray gantry (the angle of the C-arm, etc.), a determination is made as to whether there is scope to reduce the current X-ray dosage. This is because it is deduced that the operator is not performing wire manipulations and does not require fine X-ray fluoroscopy images.

The above has included descriptions of the operator sensor 33 that detects any one of the manipulated state of the wire being manipulated by the operator, the posture of the operator, the biological information of the operator, and the behavior of the operator and outputs detection results of the working state of the operator, as well as the X-ray dosage determining part 25 that uses the detection results as information for making a determination, uses a predefined threshold value as a judgment standard, and determines whether or not there is scope to reduce the current X-ray dosage.

<Method of Synthesizing Detection Results of Multiple Working States>

A method of synthesizing the detection results of multiple working states from multiple operator sensors 33 and determining an appropriate X-ray dosage will now be described. When determining the X-ray dosage, direct operations from the operator (i.e., instruction operations for stopping X-ray irradiation or for increasing or decreasing the X-ray dosage), for example, are of the highest priority, and regardless of other detection results from the operator sensor 33, it is necessary to immediately adjust the X-ray dosage in accordance with the instruction of the operator. On the other hand, high accuracy cannot be expected for appropriate X-ray dosages deduced from the respiration of the operator.

Such techniques for combining various sensors of differing levels of reliability are known, and for example, fuzzy logic may be used. In other words, a measure expressing the "dependence of the operator on the screen" or "importance of image quality" is calculated as a membership function of the fuzzy logic, and a suitable X-ray dosage is determined based thereon.

Next, an example configuration of the fuzzy logic is described. Outputs from multiple operator sensors 33 are synthesized, and the X-ray dosage determining part 25 uses image-quality importance M as information for determining whether or not there is scope to reduce the X-ray dosage. One example of a method for calculating the image-quality importance M is shown in the following formula.

[Formula 7]

$$M=(1-F)\min(1,(1-A)((1+B)/2)C+D+E) \quad (7)$$

Here, the items represented as the letters A through F are as follows.

A: This is a fuzzy truth value (Boolean value) for body motion of the operator, and is, for example, a fuzzy truth value for the standard deviation of the barycentric position of the operator detected by the pressure sensor mat described in the above seventh working-sate detection method.

B: This is a fuzzy truth value for restraint in the respiration of the operator, and is a fuzzy truth value for the standard deviation of the heart rate of the operator detected by the stethoscopic microphone described in the above eighth working-state detection method.

C: This is a fuzzy truth value for careful viewing of the display by the operator, and is, for example, a fuzzy truth value for the detection results of whether or not the operator is viewing the display that are detected by the camera described in the above third through sixth working-state detection methods.

D: This is a fuzzy truth value for changes in wire shape, and is, for example, a fuzzy truth value for the amount of change in the shape of the wire (the residual error of the mean square obtained based on the parameters θ, u, v) described in the above first working-state detection method.

E: This is a fuzzy truth value for an adaptor sensor, and is, for example, a fuzzy truth value for the frequency of wire manipulations by the operator as described in the above second working-state detection method.

F: This is a fuzzy truth value for movements of the bed and the gantry, and is, for example, a fuzzy truth value for movements of the bed, etc. detected using a position encoder of the bed and the X-ray gantry as described in the above ninth working-state detection method.

Figure 28:
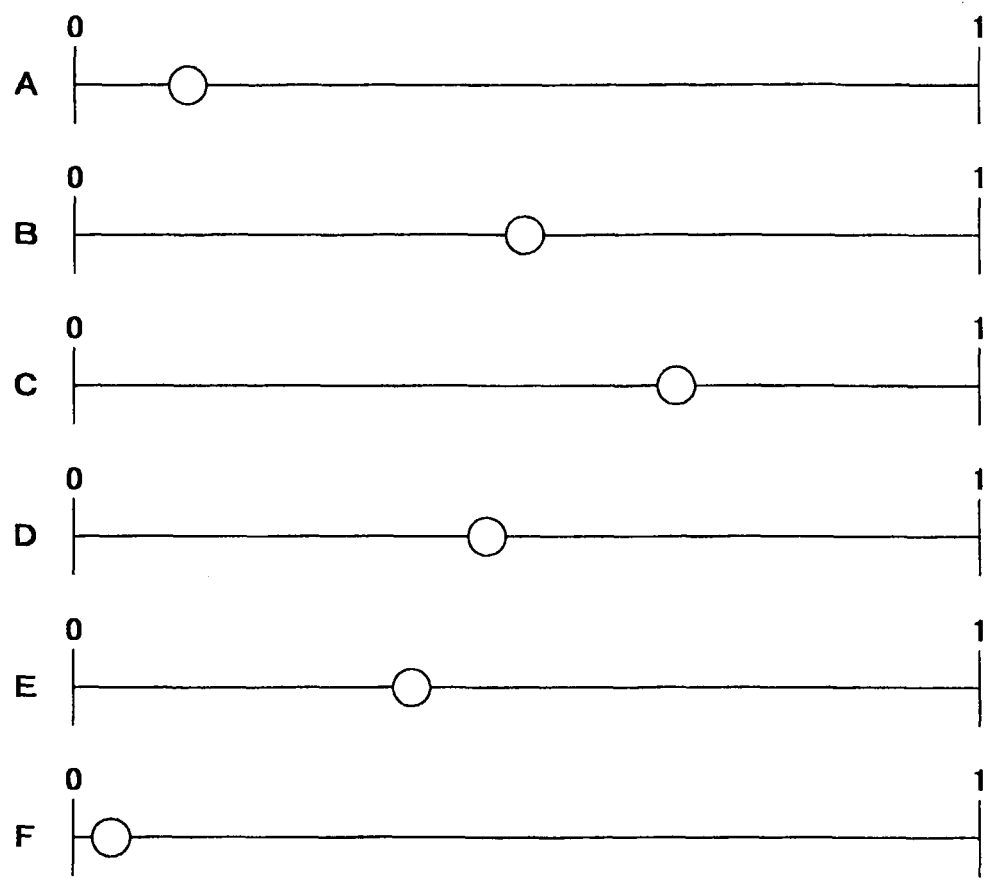
FIG. 28 is a diagram showing an example of the synthesis of multiple working-state detection results.

FIG. 28 shows the fuzzy truth values obtained for each item. The fuzzy truth value is a value from 0 to 1, and is obtained in correspondence with the detection results for each item output from the operator sensors 33.

The above has been a description of an example in which, in a system equipped with multiple operator sensors 33, outputs from multiple operator sensors 33 are synthesized using fuzzy logic, but it is also possible to aggregate predefined weights for the output results from each operator sensor 33, and use the aggregated results as information for making a determination.

Moreover, a weight database that stores combinations of weightings for output results of multiple operator sensors 33 for each operator may be provided. The system controller 21 causes the detection results of the multiple operator sensors 33 to reflect the combination of weights corresponding to the operator, and controls the X-ray dosage based on the reflected results.

The following is a description of one example of a method for creating a weight database. While making the operator perform a simulated catheterization, the working state is detected with the multiple operator sensors 33, a prescribed weight is applied to each of the items A through F, and the image-quality importance M is calculated. Here, the operator, etc. inputs a timing for allowing decreases in the X-ray dosage. The weight value is adjusted so that the timing when the image-quality importance M goes below a threshold value matches the allowance timing. By repeating the adjustment of the weight value until both timings match (when the gap between the timings is within an allowable range, for example within 1 second), a combination of weights conforming to the operator is obtained.

<Other Matters>

The following describes the manner in which the X-ray dosage is reduced if the X-ray dosage determining part 25 makes a determination to reduce the current X-ray dosage. If the X-ray dosage is reduced rapidly when it is not very clear as to whether the X-ray dosage may be reduced, this may interfere with the operations of the operator. Therefore, with the exception of cases in which there is a direct instruction, when reducing the X-ray dosage, it is appropriate to do so gradually. Moreover, if the X-ray dosage determining part 25 makes a determination to reduce the current X-ray dosage, instead of immediately starting to reduce the X-ray dosage gradually, it is preferable to start the gradual reduction of the X-ray dosage after the determination of the X-ray dosage determining part 25 continues for a while.

When the width of the irradiated region and the distance from the X-ray tube to the patient are fixed, the exposed X-ray dosage is determined based on the power input into the X-ray tube. When the voltage is lowered, the X-ray dosage is reduced, but the effectiveness of the conversion of electrical power into X-rays is also decreased. Therefore, the amount of power required outputting the same X-ray dosage increases, and the X-ray tube becomes prone to overheating. Moreover, it is difficult to implement a configuration in which the voltage may be changed rapidly due to issues of cost. When the voltage is fixed, the X-ray dosage is proportional to the product of the current, the pulse width and the frame rate. However, it is difficult to make the pulse width very narrow both technically and in terms of cost. Consequently, one economical and logical configuration is to adjust the X-ray dosage based on the current and the frame rate.

When the current (tube current) input into the X-ray tube is reduced, the X-ray dosage is reduced, the quantum noise of the X-rays and the background noise from the X-ray detector become relatively noticeable, and the image quality decreases. Therefore, it is clinically meaningless to irradiate X-rays at a tube current below a certain threshold value. If lowering the frame rate, because the X-ray dosage used to capture one frame is not changed, there is no deterioration in image quality. However, it becomes difficult to observe temporally continuous motion. Therefore, it is not desirable to lower the frame rate to an extreme degree. For example, when manipulating the bed or the X-ray gantry, this is done while viewing X-ray images in order to adjust the position to obtain an appropriate irradiated range, and a frame rate of at least around 3 fps is therefore necessary.

Next, examples of actions of the X-ray imaging apparatus are described with reference to FIG. 29. In the following description, the examples of factors for increasing and decreasing the X-ray dosage described include a pedal operation performed by the operator, movement of the bed and the X-ray gantry, and changes in wire shape, but as described for the above third through ninth working-information detection methods, it is also possible to determine whether or not the results of detecting the posture of the operator, biological information of the operator, or the behavior of the operator have exceeded their respective threshold values, and using the determination results as a factor for increasing and decreasing the X-ray dosage. Moreover, as described above, the X-ray dosage is adjusted based on the current and the frame rate.

Figure 29:
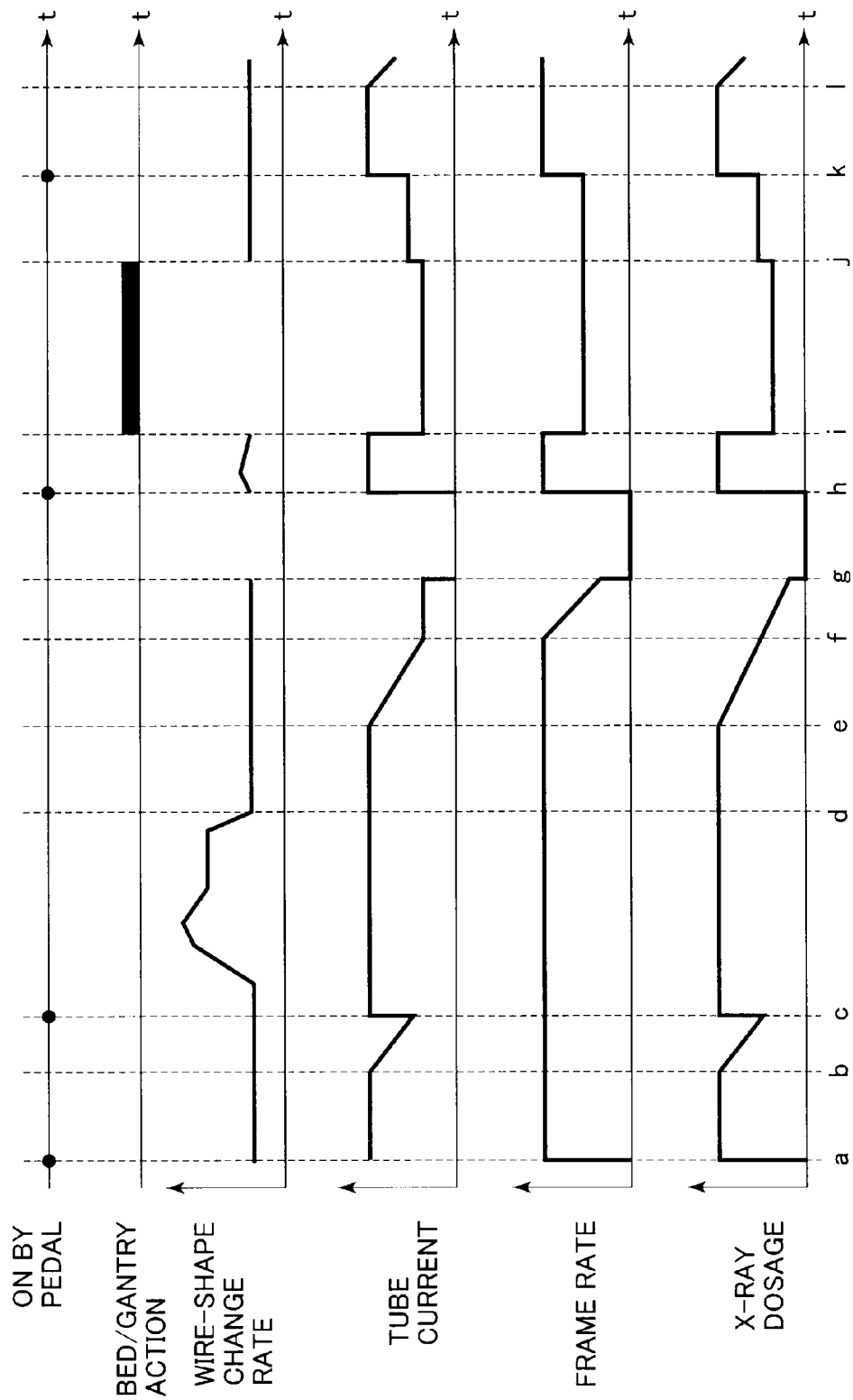
FIG. 29 is a timing chart of the amount of change in wire-shape change rate, the amount of change in tube current, the amount of change in frame rate, and the amount of change in X-ray dosage.

FIG. 29 is an example of a timing chart of an "ON" action caused by a pedal, actions of the bed and the gantry, the wire-shape change rate, the tube current, the frame rate, and the X-ray dosage. Here, an example is described in which the detection results of the amount of change in wire shape and the detection results of the amount of movement of the bed and the X-ray gantry are used as information for making a determination. In the following, the symbols a through l shown on the horizontal axis indicate time points where factors causing increases and decreases in the X-ray dosage occur (including the starting points of computation for detecting the elapsed time until the factor occurs).

With reference to FIG. 29, the time points a through l shown on the horizontal axis will now be described in order.

a: Because the operator has stepped on the pedal, X-ray irradiation is started.

b: Because the time during which changes in wire shape are small has continued for a while, the gradual reduction of X-ray dosage (tube current) is automatically started.

c: Because the operator has stepped on the pedal, the X-ray dosage is increased.

d: Because changes in wire shape are great, the high X-ray dosage is maintained.

e: Because the time during which changes in wire shape are small has continued for a while, the gradual reduction of X-ray dosage (tube current) is automatically started.

f: Because the tube current has reached a prescribed minimum value, the further gradual reduction of X-ray dosage is started by lowering the frame rate.

g: Because both the tube current and the frame rate have reached prescribed minimum values, X-ray irradiation is stopped.

h: Because the operator has stepped on the pedal, X-ray irradiation is started.

i: Because motion of the bed and the X-ray gantry has been detected, the tube current and the frame rate are lowered to reduce the X-ray dosage.

j: Because motion of the bed and the X-ray gantry has stopped, the tube current is increased to make the position easier to confirm.

k: Because the operator has stepped on the pedal, the X-ray dosage is increased.

l: Because the time during which changes in wire shape are small has continued for a while, the gradual reduction of X-ray dosage (tube current) is automatically started.

In the above examples of actions of the X-ray imaging apparatus, a means for detecting pedal operations, a means for detecting the amount of change in the shape of the wire (insert instrument), and a means for detecting motion of the bed and the X-ray gantry are used as working-state detecting means, and the X-ray dosage is controlled based on their respective detection results. However, the X-ray imaging apparatus according to the present embodiment need only control the X-ray dosage based on the detection results of multiple working-state detecting means of different types, and the working-state detecting means shown in the above examples of actions of the X-ray imaging apparatus are nothing more than examples.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF THE SYMBOLS

1: Subject
2: Top board
4: X-ray tube
6: X-ray detector
20: Arithmetic and control unit
21: System controller
22: Memory
23: Image processor
24: Display controller
25: X-ray dosage determining part
31: Display
32: Operating part
33: Operator sensor
41: Wire identifying part
43: Alignment processor

What is claimed is:

1. An X-ray imaging apparatus, comprising:
an X-ray generating means for generating X-rays and irradiating a subject with the X-rays;
an X-ray detecting means for detecting the X-rays that have penetrated said subject and capturing an X-ray image;
a working-state detecting means that detects at least one of:
information of amount of change of shape in a funicular insert instrument inserted into said subject,
information of a frequency of operations by an operator of a funicular insert instrument inserted into said subject,
information of a frequency of body motion of an operator,
information of a frequency of conversation of an operator,
information of respiration of an operator, and
information of a heart rate of an operator as a plurality of types of working-state information related to a working state of an operator performing surgery on said subject; and
an X-ray dosage control means that, based on said plurality of types of working-state information detected by said working-state detecting means, controls an X-ray dosage irradiated from said X-ray generating means.

2. The X-ray imaging apparatus according to claim 1, wherein said plurality of types of working-state information detected by said working-state detecting means includes information related to a manipulated state of an instrument inserted by said operator.

3. The X-ray imaging apparatus according to claim 1, wherein said plurality of types of working-state information detected by said working-state detecting means includes information related to amount of change of shape based on the difference between an image of said funicular insert instrument in said X-ray image and an image of said funicular insert instrument in said X-ray image captured further in the past.

4. The X-ray imaging apparatus according to claim 1, further comprising:
   a microphone;
   an adaptor,
   wherein said plurality of types of working-state information detected by said working-state detecting means includes sound information detected by the microphone provided to the adaptor for introducing said funicular insert instrument into said subject.

5. The X-ray imaging apparatus according to claim 1, further comprising:
   an acceleration sensor,
   wherein said working-state detecting means detects said plurality of types of working-state information based on detection results from the acceleration sensor attached to said operator.

6. The X-ray imaging apparatus according to claim 1, further comprising:
   a top board,
   wherein said plurality of types of working-state information detected by said working-state detecting means includes information of an amount of movement of at least one of the top board on which said subject is placed, said X-ray generating means, and said X-ray detecting means.

7. The X-ray imaging apparatus according to claim 1, further comprising:
   a display,
   wherein said plurality of types of working-state information detected by said working-state detecting means includes information about whether or not said operator is viewing the display for displaying said X-ray image.

8. The X-ray imaging apparatus according to claim 1, wherein said plurality of types of working-state information detected by said working-state detecting means includes information related to a facial orientation or line of sight of said operator.

9. The X-ray imaging apparatus according to claim 1, wherein said plurality of types of working-state information detected by said working-state detecting means includes information related to at least one of the brain waves, pupil size, frequency of blinking, amount of perspiration on the skin, or skin temperature of said operator.

10. The X-ray imaging apparatus according to claim 1, wherein, based on the detection results of said working-state detecting means, said X-ray dosage control means determines whether or not to lower the current X-ray dosage, and controls the X-ray dosage irradiated from said X-ray generating means.

11. The X-ray imaging apparatus according to claim 1, further comprising:
    an exposure switch,
    wherein, said X-ray dosage control means, when X-rays are irradiated due to an operation of the exposure switch, controls X-ray irradiation conditions related to the X-ray dosage based on said working-state information.

12. An X-ray imaging apparatus, comprising:
    an X-ray generator that generates X-rays and irradiates a subject with the X-rays;
    an X-ray detector that detects the X-rays that have penetrated said subject and capturing an X-ray image;
    processing circuitry configured to:
        detect at least one of:
            information of amount of change of shape in a funicular insert instrument inserted into said subject,
            information of a frequency of operations by an operator of a funicular insert instrument inserted into said subject,
            information of a frequency of body motion of an operator,
            information of a frequency of conversation of an operator,
            information of respiration of an operator, and
            information of a heart rate of an operator as a plurality of types of working-state information related to a working state of an operator performing surgery on said subject, and
        control an X-ray dosage irradiated from said X-ray generator based on said plurality of types of working-state information.

* * * * *